(12) United States Patent
Saim et al.

(10) Patent No.: US 6,858,166 B2
(45) Date of Patent: Feb. 22, 2005

(54) POWDER PROCESSING WITH PRESSURIZED GASEOUS FLUIDS

(75) Inventors: Said Saim, New Milford, CT (US); Stephen Horhota, Brookfield, CT (US); Kenneth James Koenig, New Milford, CT (US); David Joseph Bochniak, Southbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 113 days.

(21) Appl. No.: 10/268,879

(22) Filed: Oct. 10, 2002

(65) Prior Publication Data

US 2003/0066800 A1 Apr. 10, 2003

Related U.S. Application Data

(60) Provisional application No. 60/328,301, filed on Oct. 10, 2001.

(51) Int. Cl.$^7$ .............................. B29B 9/00; B01J 2/00; B01J 3/00
(52) U.S. Cl. ............................... 264/5; 210/634; 239/8; 239/10; 264/7; 264/12; 424/489; 424/490; 427/212
(58) Field of Search ................................ 210/634, 638; 264/5–9, 12–14; 427/212, 213, 421, 422; 239/8–10; 424/489–491, 451, 499

(56) References Cited

U.S. PATENT DOCUMENTS

| | | |
|---|---|---|
| 4,582,731 A | 4/1986 | Smith |
| 4,734,451 A | 3/1988 | Smith |
| 4,828,702 A | 5/1989 | Coenen et al. |
| 4,970,093 A | 11/1990 | Sievers et al. |
| 5,043,280 A | 8/1991 | Fischer et al. |
| 5,290,604 A * | 3/1994 | Nielsen ....................... 427/421 |
| 5,301,664 A | 4/1994 | Sievers et al. |

(List continued on next page.)

FOREIGN PATENT DOCUMENTS

| | | |
|---|---|---|
| WO | WO 95/01221 A1 | 1/1995 |
| WO | WO 98 17676 | 4/1998 |
| WO | WO 98 52544 | 11/1998 |
| WO | WWO01/45674 | * 6/2001 |

OTHER PUBLICATIONS

Tan, H. S. et al; "Particle formation using supercritical fluids: pharmaceutical applications"; Expert Opinion on Therapeutic Patents; 2001, 11, pp. 861–872.

Larson, K. A. et al; "Evaluation of Supercritical Fluid Extraction in the Pharmaceutical Industry"; Biotechnology Progress 2(2), Jun. 1986, pp. 73–82.

Yeo, et al; "Formation of Microparticulate Protein Powders Using a Supercritical Fluid Antisolvent"; Biotechnology and Bioengineering, 1993, vol. 41, p. 341–346.

Subramaniam, B. et al; "Green Process Concepts for the Pharmaceutical Industry"; Green Engineering, ACS Symposium Series 766, Ch. 8, 2001, pp. 96–110.

*Primary Examiner*—Joseph Drodge
(74) *Attorney, Agent, or Firm*—Michael P. Morris; MaryEllen M. Devlin; Philip I. Datlow

(57) ABSTRACT

Disclosed is a method of small particle precipitation, retention and dispersion of a solid or semi-solid material onto or into a carrier material. In this method, solute particles are precipitated from a pressurized gaseous fluid solution or a liquid solution and effectively retained and dispersed within a carrier material. This technique can be advantageously used in pharmaceutical processing to produce a blend of solid or semi-solid material particles and carrier material, a granulation of the solid or semi-solid material particles with carrier material, carrier material partially or fully coated with the solid or semi-solid material particles, or mixtures thereof.

26 Claims, 21 Drawing Sheets

U.S. PATENT DOCUMENTS

| | | |
|---|---|---|
| 5,360,478 A | 11/1994 | Krukonis et al. |
| 5,374,305 A | 12/1994 | Glancy et al. |
| 5,389,263 A | 2/1995 | Gallagher et al. |
| 5,639,441 A | 6/1997 | Sievers et al. |
| 5,707,634 A | 1/1998 | Schmitt |
| 5,770,559 A | 6/1998 | Manning et al. |
| 5,795,594 A | 8/1998 | York et al. |
| 5,803,966 A | 9/1998 | Kulshreshtha et al. |
| 5,833,891 A | 11/1998 | Subramaniam et al. |
| 5,851,453 A | 12/1998 | Hanna et al. |
| 5,874,029 A | 2/1999 | Subramaniam et al. |
| 6,063,138 A | 5/2000 | Hanna et al. |
| 6,063,910 A | 5/2000 | Debenedetti et al. |
| 6,087,003 A | 7/2000 | Benoit et al. |
| 6,248,363 B1 * | 6/2001 | Patel et al. .................. 424/497 |
| 6,461,642 B1 | 10/2002 | Bisrat et al. |
| 2001/0055561 A1 | 12/2001 | Siam et al. |
| 2004/0091546 A1 * | 5/2004 | Johnson et al. |

\* cited by examiner

POWDER PROCESSING WITH PRESSURIZED GASEOUS FLUIDS

This application claims the benefit of prior U.S. provisional application No. 60/328,301, filed on Oct. 10, 2001, and said prior application is herein incorporated by reference in its entirety.

FIELD OF THE INVENTION

This application generally relates to a method that employs a pressurized gaseous fluid for processing out of solution particles of a solid or semi-solid material for simultaneously retaining and dispersing these processed particles in a carrier material. This technique can be advantageously used in pharmaceutical and chemical processing to produce a blend of the solid or semi-solid material particles and carrier material, a granulation of the solid or semi-solid material particles with carrier material, carrier material partially or fully coated with the solid or semi-solid material particles, or mixtures thereof.

BACKGROUND OF THE INVENTION

Solid dosage forms for pharmaceuticals such as tablets and capsules require the use of fine powders of drug substance material in order to achieve uniform distribution of the pharmacologic agent in these powder-based formulations. Additionally, drug substances with very low solubility and dissolution rates often need to be reduced in size to levels on the order of 10 $\mu$m or less in order to achieve satisfactory bioavailability. In some cases, particles <1 $\mu$m are necessary for drugs with exceptionally poor aqueous solubility.

Conventional techniques for the processing of drug substance particles from solutions suffer from many disadvantages. Recrystallization, freeze drying and spray drying require solvent evaporation. Drying techniques can leave residual amounts of solvent and the use of heat to aid drying can cause thermal degradation of the drug substance. Mechanical milling to reduce particle size can also cause thermal degradation. All of these techniques can result in particle size variability.

Improved methods for generating micron and sub-micron size particles with narrow particle size distribution using supercritical fluids (SCFs) such as $CO_2$ have been disclosed (see for example U.S. Pat. No. 5,833,891 and H. S. Tan and S. Borsadia, Expert Opinion on Therapeutic Patents, 2001, 11, 861-872). Methods include Supercritical Fluid Extraction (SFE), Rapid Expansion of Supercritical Solutions (RESS), Gas Anti-Solvent Recrystallization (GAS), as well as Supercritical fluid Antisolvent (SAS).

A supercritical fluid (SCF) is a substance above its critical temperature and critical pressure (31° C., 1,070 psi for $CO_2$). A SCF such as $CO_2$ is essentially a compressed, high diffusivity and high density fluid at mild temperature. It is relatively innocuous, inexpensive, and unreactive. SFE is often used to selectively extract a variety of compounds. After extraction, the SCF mixture is expanded into a collection vessel held at a lower pressure. Because of the low solvent power of the low-pressure gas, the compound precipitates and is collected in a vessel. The effluent low pressure gas is vented out or recycled into the process. A wealth of information on the properties of SCFs is available in the technical literature (McHugh, M. and Krukonis, V., Supercritical Fluid Extraction, Principles and Practice, $2^{nd}$ Ed., Butterworth-Heinemann, Boston. 1993).

At the heart of every particle formation technique utilizing SCFs is their ability to dissolve in or solubilize a particular solvent or substance. Although SFE has been used to produce pharmaceutical powders (Larson, K. A. et al., Biotechnology Progress 2 (2), June 1986, pp. 73–82), it is normally used for selective extraction of SCF-soluble material from raw substrates where the particle size of the extracted material following depressurization is generally not a concern of the process. A particularity of SFE is that it can be used to extract desirable materials as well as impurities in any physical form: liquid, solid or semisolid.

The concept that material dissolved in a SCF can be precipitated by rapid reduction in pressure has been known for over a century (J. B. Hannay and J. Hogarth, "On the solubility of solids in gases", Proceedings of the Roy. Soc. London, 29, 324–326, 1879). The RESS process (U.S. Pat. No. 4,582,731) takes advantage of this property of SCFs to crystallize desirable solid substances for which particle size and possibly other physical and bulk characteristics are a main concern.

In the RESS process, similar to SFE, a solute substance is placed in a high-pressure vessel. A SCF is then pumped through the vessel to dissolve the substance and form a solution of the substance in the SCF. The fluid mixture is then expanded through a nozzle into a vessel held at a substantially lower, sub-critical pressure where the fluid is now a low density gas. Because of the low solvent power of the low-pressure gas, the substance precipitates and is collected in the vessel. The large pressure differential across the nozzle causes the expansion to take place at ultrasonic velocity and supersaturation to increase rapidly. The rapid expansion translates into a rapid change in the density and solvent power of the fluid and therefore into rapid crystallization rates which result in the formation of small microparticles and nanoparticles of the substance. Effluent gas is passed through a micro-filter and then vented or recycled. An alternative way to rapidly reduce the solvent power of the SCF without any substantial change in pressure consists of contacting the SCF solution with an inert gas such as nitrogen or helium where the solute substance is substantially insoluble. The inert gas may be kept at a pressure similar to that of the SCF solution. The inert gas rapidly mixes with the SCF to cause its solvent power to decrease and the solute to precipitate.

For material that has little solubility in a SCF of choice, the SCF may be used as an antisolvent. The GAS process (U.S. Pat. No. 5,360,478; U.S. Pat. No. 5,389,263) was first reported at an international meeting of the American Institute of Chemical Engineers (Paper 48c at the AIChE Meeting, Nov. 29, 1988) and later by Gallagher, P. M. et al. (Chap 22, Supercritical Fluid Science and Technology, ACS Symposium Series, 406, Washington, D.C., K. P. Johnston, J. M. L. Penninger, ed., ACS Publishing, 1989). In GAS, a SCF is used as an antisolvent to process a SCF-insoluble solute from a pre-mixed batch of an organic solution of the solute by adding a SCF into the solution. Addition of the SCF causes its concentration in the solution to increase and the solution to expand. Solute precipitation takes place when the solution becomes supersaturated.

The batch GAS process is limited in its ability to process large quantities of material. In the SAS process, the organic solution of the solute is added continuously to continuously flowing SCF antisolvent. The organic solvent rapidly mixes and dissolves in the SCF to form a homogeneous high-pressure fluid mixture. Because the solute is substantially insoluble in the SCF and the SCF and the organic solvent are miscible, this results in its precipitation in the high pressure vessel. The SCF-organic solvent mixture is passed through a micro-filter and then expanded into a low pressure vessel where the SCF separates from the organic solvent.

Because of the relatively low processing temperature, the SAS process is suitable for processing thermally labile substances. Unlike other processes such as conventional spray drying where the rate of solvent removal from droplet surfaces is relatively slow and depends to a large extent on processing temperature, in this process such rate depends primarily on the density and flow rate of the SCFs. Both parameters can easily be controlled over a wide range at a relatively low temperature to control the rate of solvent removal over an equally wide range. Several variants of the SAS process have been developed. Coenen et al. (U.S. Pat. No. 4,828,702) report a countercurrent process whereby a liquid solution of a solid solute is sprayed into a SCF antisolvent such as $CO_2$ to recover the solid material as a powder. Fisher and Muller (U.S. Pat. No. 5,043,280) report a process whereby a liquid solution of active substance is sprayed as a fine mist into a SCF solution of a carrier material to produce sterile microparticles of active substance embedded within carrier material. Yeo et al. (Biotechnology and Bioengineering, 1993, Vol. 41, p. 341) and Debenedetti (U.S. Pat. No. 6,063,910) also describe a process whereby the solution is sprayed as a fine mist across a nozzle into a high pressure vessel containing a SCF in order to produce fine powders of the solute. Schmidt (U.S. Pat. No. 5,707,634) reports a process whereby a non-sterile solute is recovered from a solution injected into a high-pressure vessel containing a SCF antisolvent. Subramaniam et al. (U.S. Pat. No. 5,833,891) describe a process whereby an ultrasonic nozzle is used to enhance the atomization of the liquid solution spray which aids in the production of finely divided microparticles and nanoparticles of active material.

The SAS process has also been identified in the literature as "Aerosol Solvent Extraction Systems" (ASES) and a variation thereof has been identified as "Solution-Enhanced Dispersion by SCFs" (SEDS). See Tan and S. Borsadia, Expert Opinion on Therapeutic Patents, 2001, 11, 861–872.

SEDS (U.S. Pat. Nos. 5,851,453 and 6,063,138) involves using a coaxial, non-ultrasonic nozzle. High mass transfer rates are achieved with a high ratio of supercritical fluid to solvent and the high velocities of the SCF facilitate the atomization of the solution. Particles produced using SCFs have also been used to coat substrates. Subramaniam et al. (U.S. Pat. No. 5,833,891) describe a process whereby particles are crystallized from a liquid solution and directed at a bed of fluidized core particles to form a coating. In this process, the SCF is used to both fluidize the core particles and to effect the crystallization of the coating substance out of the solution. The process can be used in a manner similar to the classic Wurster coating process. Benoit et al. (U.S. Pat. No. 6,087,003) describe a batch process whereby an active substance is stirred in a high pressure vessel containing a SCF and a coating material dissolved therein. The temperature of the SCF is then gradually lowered to a point where it separates into a gas phase and a liquid phase where the core particles are in suspension and the coating material is in solution. Continuous removal of the gas phase causes the concentration of the coating material in the liquid phase to increase and its solubility to decrease. This results eventually in the precipitation of the coating material on the active substrate. Because of the possibly limited solubility of coating material in a batch of SCF, the process may be repeated using pre-loaded coating material attached to the shaft of the stirring device. Smith (U.S. Pat. No. 4,582,731) discusses a process whereby particles formed by RESS are directed at and adhered to solid surfaces such as glass, fused silica and platinum to form a thin film coating.

Processes described above are designed to produce either coated substrates or microparticles or microcapsules of a particular substance. A premise for the present invention is that in the pharmaceutical industry, fine drug powders are rarely used as final solid state formulations because collection, handling, flow, and/or compression of powders of microparticles and nanoparticles can be very challenging. A micronized powder of a particular drug substance is therefore rarely used without further processing. If one desires to make a solid state pharmaceutical formulation of a drug substance, it is generally necessary to mix the drug microparticles or nanoparticles with particles of carrier substance (s). Such carriers, such as lactose, exhibit good handling, flow, and compression properties. After mixing with a carrier, granulation is often used in the pharmaceutical industry to produce free-flowing, dust-free granules from fine powders and to improve the uniformity of drug distribution in the product (Handbook of Pharmaceutical Granulation Technology, Marcel Dekker, N.Y., Dilip, M. P. Editor, Vol. 81, 1997). Current processes using SCFs to process fine powders do not address these issues. The following are some limitations of current processes:

1. Current processes do not address the difficulty of trapping fine particles upon their formation. They are designed to precipitate discrete small microparticles and nanoparticles which are normally difficult to trap in a processing vessel. Retention of such particles on filters is difficult and may result in filter plugging and/or reduction in throughput.
2. Current processes do not address the issues associated with the tendency of fine powders to agglomerate. In the SAS process, where particles crystallize rapidly, wet particles may come in close contact with each other and fuse or agglomerate. Similarly, in RESS, semi-solid or adhesive particles cannot be satisfactorily processed because they would rapidly agglomerate. Irrespective of the physical characteristics of the material, microparticles and nanoparticles of material exhibiting high surface free energy will tend to agglomerate and fuse to form large particles when in close contact. When processing drug substances, agglomeration can increase the effective particle size and result in lower drug dissolution rate and bioavailability. Agglomeration of crystallized material limits its effectiveness for coating small micron- and nanometer-sized particles. The utility of current processes is therefore limited in this regard.
3. Current processes designed to coat core particles with precipitated fine powders in a fluidized bed are difficult to control. Such processes do not address fine particle retention or the ability to coat fine powders which are notoriously difficult to fluidize. Fluidized beds require special equipment and controls that are not easily amenable for use with SCFs. The purpose of fluidizing the core particles is to suspend them so that they may be coated and dried preferably before coming in contact with another core particle, thereby minimizing agglomeration. Coating of core particles by this process can be achieved for many powders, but normally may require a great deal of process control. Specialized fluidization equipment normally does not allow for stirring but provides for a carefully controlled pressure differential within the vessel to effect fluidization of particles, uniform distribution of the fluidizing gas, control of bed expansion, and collection of fines. The superficial velocity of suspending fluid is critical; too high a velocity will cause the core particles to become entrained onto the filter; too low a velocity may result in incomplete expansion/fluidization of the bed. Because precipitation and drying happens very quickly in SCF processing, the droplets may be dried prior to contacting the core particles and the very small crystals that are produced can easily be entrained in the suspending fluid. Therefore, precipitation with adhesion to the core particles may not occur consistently, and some precipitated particles may become separated from the bed of core particles. The expansion and fluidization of a powder bed also requires longer and larger processing vessels, a major concern with high pressure equipment. Some powders may be more difficult to fluidize because of the enormous number of possible particle-particle interactions and changes in bed properties such as particle size distribution as particles are formed and others are coated. Core particles smaller than 10 μm often form unstable fluidized beds. Small particles may act as if damp, forming agglomerates or fissures which may result in spouting. Such processing difficulties are at least partially responsible for the limited use that fluidized bed processing has found in pharmaceutical processing. The technical literature provides a full account of the problems associated with fluid bed processing of small particles.

A drawback of RESS, GAS and SAS processes is the difficulty of trapping, collecting and handling fine powders of microparticles and nanoparticles. Filters used in these processes are generally not capable of effectively retaining the produced microparticles and nanoparticles. If filter pores are small enough to retain such particles, the filter can become rapidly plugged up by the particles. This can severely restrict flow through the crystallization vessel, and frequent interruptions to clean or replace filters may become necessary. In the case of RESS, resistance to flow causes pressure in the vessel to rise appreciably and the pressure drop across the nozzle to decrease. At some point, the pressure drop vanishes completely and the process would need to be halted. In the case of SAS, resistance to flow could also cause pressure in the vessel to continuously rise throughout the process. Even if microparticles can be retained by such devices as cyclones, they present handling difficulties. Flow characteristics of powders containing microparticles and/or nanoparticles are generally poor. Such powders may therefore be difficult to discharge and use in downstream processes. Further processing by such processes as mixing with carrier material and granulation may therefore still be necessary before incorporation into a formulation. Powders with poor flow characteristics are difficult to incorporate into carrier material and normally require special blending procedures or techniques to obtain the required blend uniformity. Fine powders are also difficult to handle because of their dustiness. Special operator protection is required and very specific procedures are required for potent drugs or toxins.

SUMMARY OF THE INVENTION

The present invention is in general directed to a method for solute particle precipitation, retention and dispersion in a carrier material by taking advantage of the unique properties of pressurized gaseous (e.g. supercritical) fluids to precipitate solute particles from solution and by effectively retaining and dispersing the precipitated particles in a carrier material having good flow and handling properties. A solute may be precipitated from either a liquid solvent or a pressurized gaseous fluid solution. As described herein, this process has broad applicability in the pharmaceutical industry.

In general, the method of the present invention involves:
(a)(1) dissolving a solid or semi-solid material in a pressurized gaseous fluid, thereby forming a solution comprising a gaseous fluid solvent and a dissolved solute of solid or semi-solid material or (a)(2) dissolving a solid or semi-solid material in a liquid solvent, thereby forming a solution comprising a liquid solvent and a dissolved solute of solid or semi-solid material;

(b)(1) precipitating particles of the solid or semi-solid material out of the gaseous fluid solution produced in step (a)(1) by introducing the solution into a region of lower pressure or into a region containing an inert gas or (b)(2) precipitating particles of the solid or semi-solid material out of the liquid solution produced in step (a)(2) by introducing the solution into either: (1) a region containing a pressurized gaseous fluid in which said liquid solvent is substantially soluble but said solid or semi-solid material is substantially insoluble, or (2) a region into which said pressurized gaseous fluid is subsequently introduced to cause the solubilization of the liquid solvent into the pressurized gaseous fluid and the precipitation of the particles of the solid or semi-solid material;

(c) directing the introduced solution and resulting precipitated particles produced in step (b)(1) or (b)(2) onto or into a mixed bed of carrier material; and (d) retaining and dispersing at least some of the precipitated particles in the carrier material to produce a blend of the solid or semi-solid material particles and carrier material, a granulation of the solid or semi-solid material particles with carrier material, carrier material partially or fully coated with the solid or semi-solid material particles, or mixtures thereof.

The present method is applicable to the precipitation (or crystallization) of a wide variety of solid and semi-solid materials, e.g., physiologically active materials, encapsulating materials, moisture protection materials, light protection materials, gas protection materials, diffusion barrier materials, and dissolution or dispersion enhancing materials, and the retention and dispersion thereof using a wide variety of carrier materials, e.g., pharmaceutically acceptable carriers, adjuvants or excipients, or physiologically active materials, or mixtures thereof. The present method is particularly advantageous for the precipitation, retention and dispersion of microparticles and nanoparticles of solid or semisolid material within a carrier material.

The blends, granulations and partially or fully coated carrier materials, or mixtures thereof, produced by the methods of the present invention are particularly suited for pharmaceutical processing into various pharmaceutical formulations and dosage forms, such as tablets and capsules. Carrier material with good flow characteristics is generally used in the formulation of most solid dosage forms. Its presence in admixture with the drug is therefore an advantage. Blend uniformity can be achieved even when drug content is very small because drug powder is not handled separately from the excipients and can adhere to excipient particles during its manufacture.

Other advantages of the inventive method include the following:

1. If drug-loading in the carrier material is not too high, the particle size distribution of the processed powder may be close to that of the carrier material itself prior to processing. Flow characteristics of the processed powder may therefore be as good as those of the carrier itself. This reduces difficulties in discharging and in handling the powder in downstream processing.

2. The carrier may be coated with drug substance followed by coating with an encapsulating material. The procedure may be repeated to increase drug loading preferably without causing substantial agglomeration between drug particles to take place. The coatings could also be of a type to offer moisture, light or gas barriers for drugs that are chemically sensitive to water or oxygen or are photosensitive. The coatings could also be of the type that serve as diffusion barriers to control the release of the drug substance from the substrate or as a dissolution or solubility enhancer.
3. This invention is not limited to powders. It may be employed, for example, in blending crystallized microparticles and nanoparticles with larger sized material or for coating of granules, pellets, non-pareils, tablets, capsules or other mixed material. The method can equally be used to form a granulation of the solid or semi-solid material particles with the carrier material.

The invention may be used in various ways, including but not limited to:
1. Producing a uniform blend of discrete or loosely adhered drug microparticles and nanoparticles and carrier material.
2. Producing a uniform blend of discrete or loosely adhered carrier particles and drug material.
3. Producing a granulation of drug microparticles and nanoparticles with carrier material. A binder such as polyvinyl pyrrolidone (PVP) may be present either in admixture with a drug substance in the liquid or gaseous fluid solution or in admixture within the carrier powder bed.
4. Coating of a drug substance with a coating material. The coatings could also be of a type to offer moisture, light or gas barriers for drugs that are chemically sensitive to water or oxygen or are photosensitive. The coatings could also be of the type to serve as diffusion barriers to control the release of the drug substance from the substrate or to enhance its release.
5. Coating of a carrier with a drug substance followed by coating with an encapsulating material. The procedure may be repeated to increase drug loading preferably without causing substantial agglomeration between drug particles.

BRIEF DESCRIPTION OF THE DRAWINGS

FIG. 7A is at 40× magnification; FIG. 7B is at 200× magnification; and FIG. 7C is at 5,000× magnification.

FIG. 8A is at 40× magnification; FIG. 8B is at 200× magnification; and FIG. 8C is at 5,000× magnification.

FIG. 9A is at 40× magnification; FIG. 9B is at 500× magnification; and FIG. 9C is at 5,000× magnification FIG. 10A is at 40× magnification; FIG. 10B is at 200× magnification; and FIG. 10C is at 5,000× magnification

FIG. 12 is at 40× magnification; FIG. 13 is at 500× magnification; FIG. 14 is at 2,000× magnification; and FIG. 15 is at 5,000× magnification.

FIG. 16 is at 5,000× magnification.

FIG. 17 is at 500× magnification; FIG. 18 is at 5,000× magnification; and FIG. 19 is at 10,000× magnification.

DETAILED DESCRIPTION OF THE INVENTION

Figure 1:
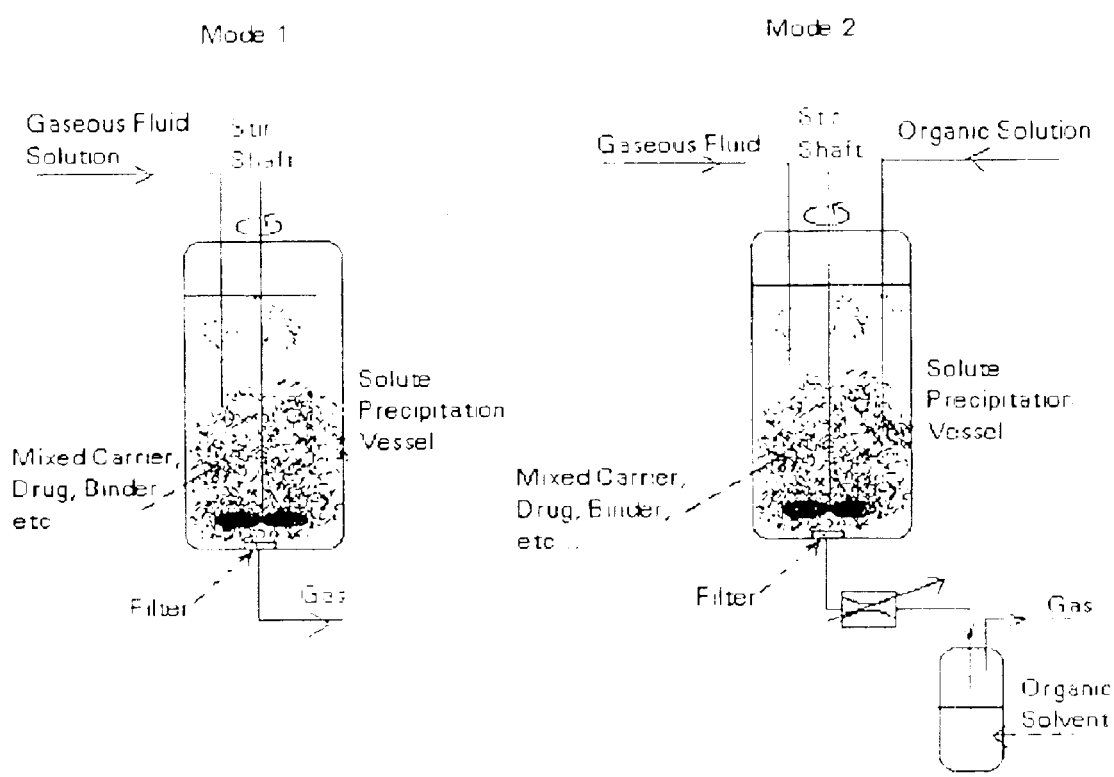
FIG. 1 depicts simplified flow diagrams showing two specific embodiments of Modes 1 and 2 of the present invention.
Figure 2:
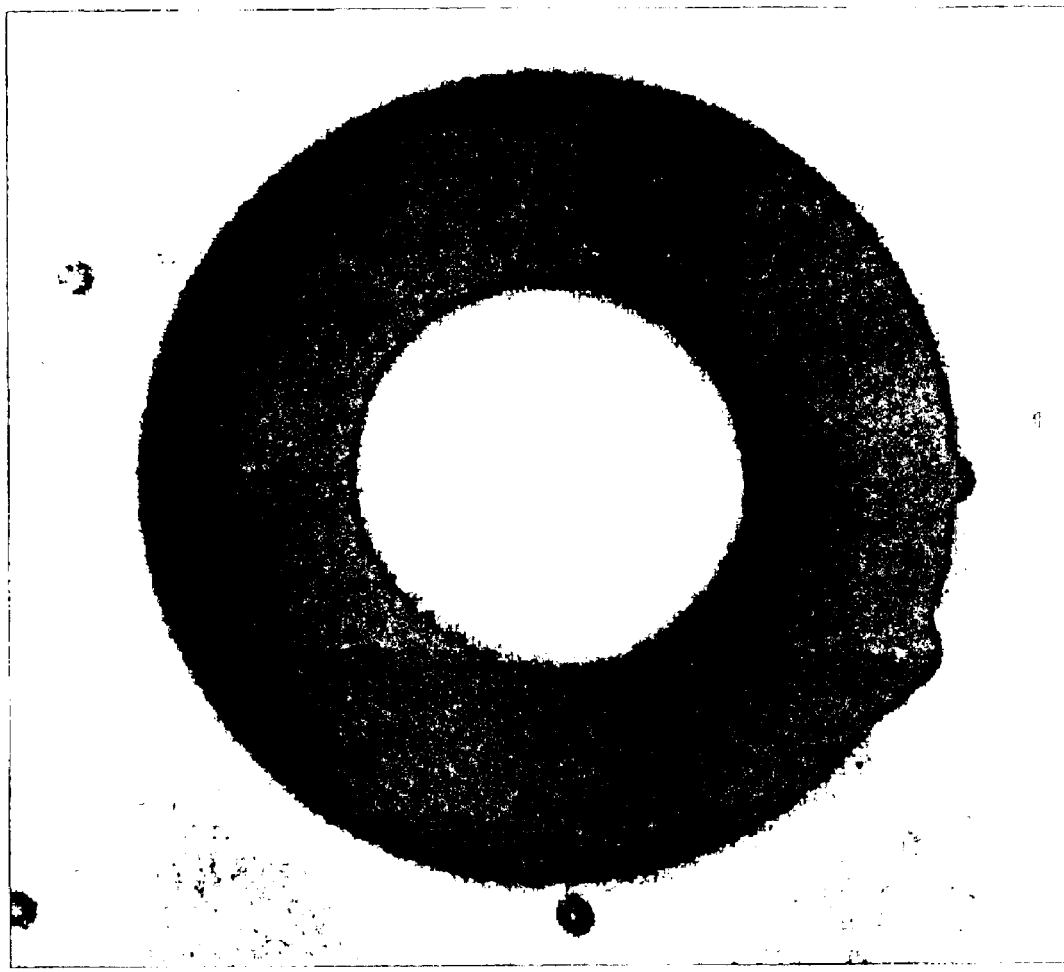
FIG. 2 is a light microscopy image of polystyrene divinyl benzene micro-bead subjected to supercritical $CO_2$ at 50° C. and 1,000 psig.
Figure 3:
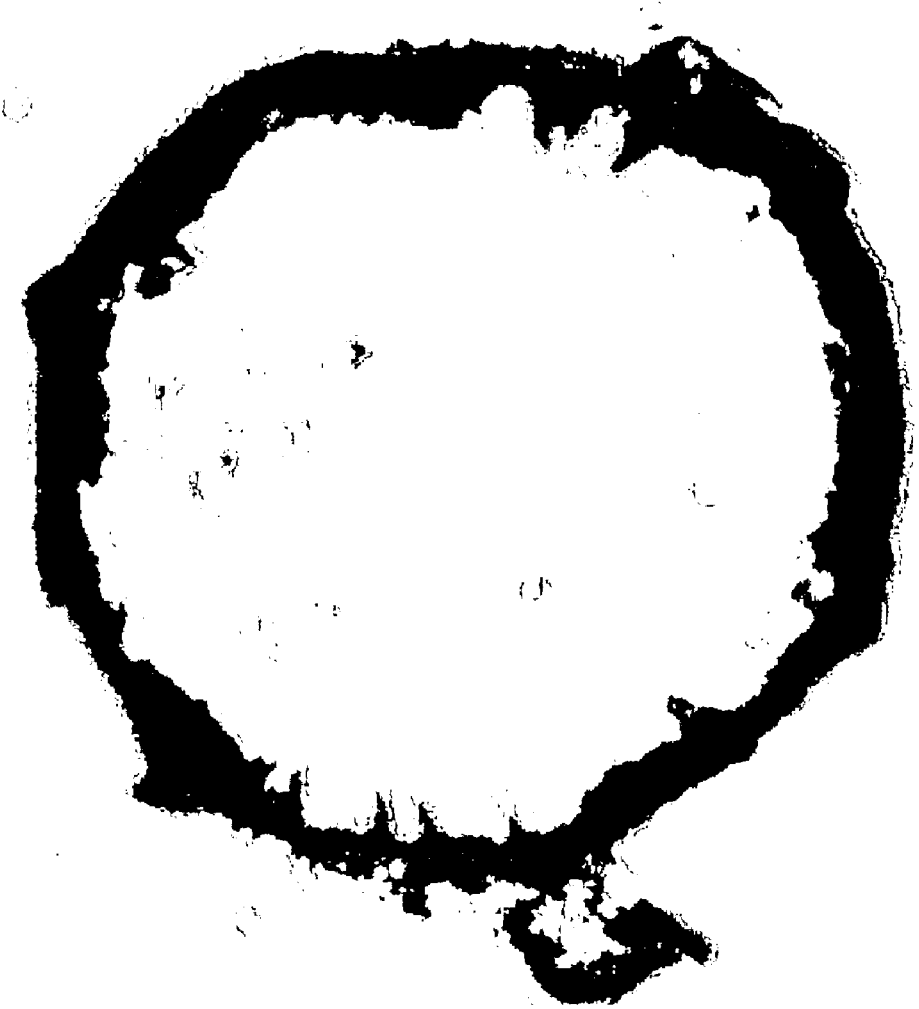
FIG. 3 is a light microscopy image of a polystyrene divinyl benzene micro-bead upon which recrystallized drug substance has been deposited using a method of the present invention wherein the drug substance was recrystallized from a supercritical $CO_2$ solution.
Figure 4:
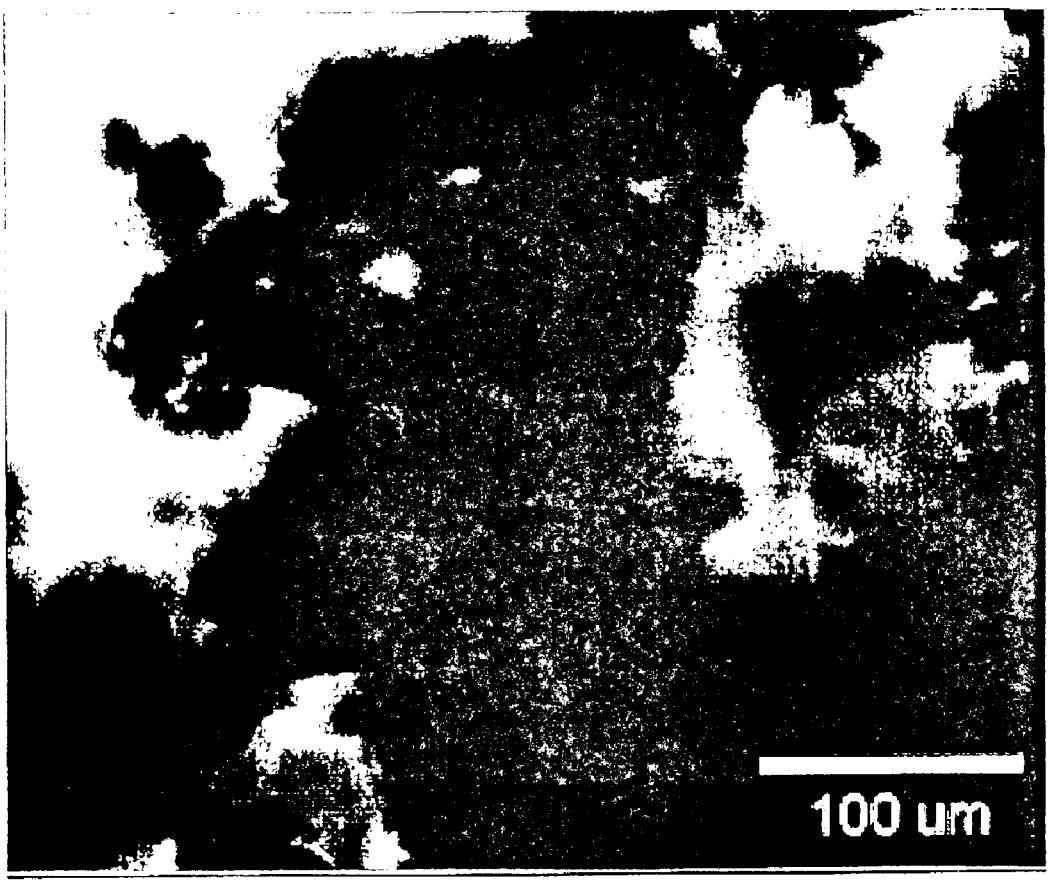
FIG. 4 shows the bright field (tungsten) illumination of a group of lactose particles upon which recrystallized drug substance has been deposited using a method of the present invention wherein the drug substance was recrystallized from a supercritical $CO_2$ solution.
Figure 5:
FIG. 5 shows the UV illumination (high pressure mercury lamp) of a group of lactose particles upon which recrystallized drug substance has been deposited using a method of the present invention wherein the drug substance was recrystallized from a supercritical $CO_2$ solution.
Figure 6:
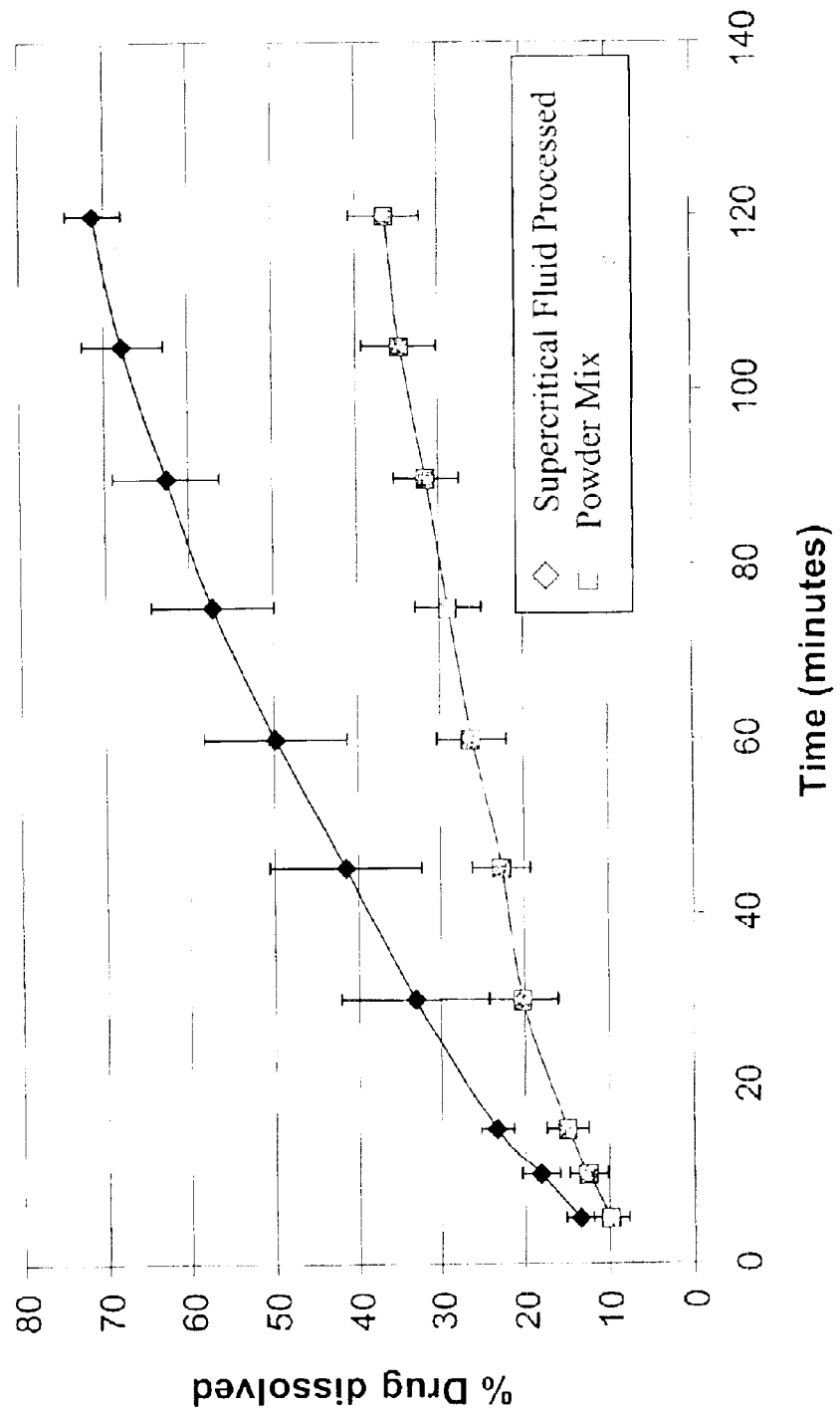
FIG. 6 shows the dissolution profile of a drug-lactose mixture obtained by supercritical $CO_2$ processing of the drug substance using a method of the present invention as compared to the dissolution profile of a drug-lactose mixture obtained by conventional physical mixing of the drug and lactose.

All terms as used herein in this application, unless otherwise stated, shall be understood in their ordinary meaning as known in the art. Other more specific definitions for certain terms as used in the present application are as set forth below:

By the term "about" with respect to a recited value is meant ±20% of the recited value, preferably ±10%, more preferably ±5%, even more preferably ±1%. When the term "about" is used in relation to a range of values, the term "about" is intended to qualify each recited end-point of the range. For example, the phrase "about 0.8 to 1.6 $T_c$" is equivalent to "about 0.8 to about 1.6 $T_c$."

By the term "blend" is meant a uniform or non-uniform mixture.

By "pressurized gaseous fluid", or "supercritical fluid" is meant (1) a fluid or mixture of fluids that is gaseous under atmospheric conditions and that has a moderate critical temperature (i.e., $\leqq 200°$ C.), or (2) a fluid that has previously found use as a supercritical fluid. Examples of gaseous fluids include carbon dioxide nitrous oxide, trifluoromethane, ethane, ethylene, propane, sulfur hexafluoride, propylene, butane, isobutane, pentane, and mixtures thereof. Unless explicitly stated, the temperature and pressure of the gaseous or supercritical fluid can be anywhere in the near-critical to supercritical region, e.g., in the range of about 0.8–1.6 $T_c$ and about 0.8–15 $P_c$ where $T_c$ and $P_c$ are, respectively, the critical temperature in K and the critical pressure of the fluid.

By "microparticles" is meant particles having a average particle diameter in the range of about 1 to 500 $\mu$m, preferably in the range of about 1 to 10 $\mu$m.

By "nanoparticles" is meant particles having an average particle diameter in the range of about 0.001 to 1 $\mu$m, preferably in the range of about 0.05 to 0.5 $\mu$m.

By "mixed bed" with respect to the carrier material is meant a non-fluidized mixture of carrier material, in the absence or presence of precipitated particles of the solid or semi-solid material. A mixed bed of carrier material can be formed, for example, by stirring or agitating the carrier material in the absence or presence of precipitated particles of the solid or semi-solid material.

By "non-fluidized" with respect to the carrier material is meant that the carrier material in the mixed bed is not in a gas-suspended fluidized state. For example, the mere stirring or agitating of the carrier material in the bed during the process of the present invention may have the effect of expanding at least some of the carrier material bed, but this is not gas-suspended fluidization of the carrier material.

The terms "precipitation" or "precipitating" mean the process of forming crystalline or amorphous particles of solute, or mixtures thereof, out of solution. Thus, these terms are intended to include within the context of the present invention the concept of crystallization of dissolved solute out of solution. When a mixture of solutes (e.g., solid or semi-solid materials) are dissolved in solution, the concept of "precipitation" or "precipitating" particles of material in the context of the present invention includes the possibilities that not all the dissolved solutes are precipitated and/or that a solute may precipitate only partially out of solution. Thus, the precipitation process of the present invention may be used to separate certain solid or semi-solid materials.

By "RESS" is meant a process whereby solute particles are precipitated from a gaseous fluid solution of the solute by either expanding the solution in a lower pressure region or contacting the solution with an inert gas at the same pressure as the gaseous fluid or at lower pressure.

By "semi-solid" is meant a solid material that possesses at least some liquid-type physical characteristics. Examples of semi-solid materials include: gels, viscous liquids, oils, surfactants, polymers, waxes, and fatty acids.

By the term "semi-solid material" is meant one or more substances that are semi-solid at ambient or process conditions. Thus, the language "a semi-solid material" is intended to include the possibility that the semi-solid material is a mixture of different semi-solid materials.

By the term "solid material" is meant one or more substances that are solid at ambient or process conditions. Thus, the language "a solid material" is intended to include the possibility that the solid material is a mixture of different solid materials.

By the term "process conditions" is meant the specific conditions under which a process of the present invention is run.

By the term "substantially soluble", e.g., with respect to the solubility of the liquid solvent in the gaseous fluid, is meant that under selected processing conditions the liquid solvent can be completely solubilized by the gaseous fluid with the exception of residual liquid solvent contamination that may be present on the carrier material particles. Quantitatively, it is preferable that at least about 95%, more preferably at least about 99%, of the liquid solvent is solubilized in the gaseous fluid.

By the term "substantially insoluble", e.g., with respect to the solubility of the solid or semi-solid material in the gaseous fluid in Mode 2, is meant that under selected processing conditions the solid or semi-solid material should be no more than about 50% by weight soluble, preferably no more than about 25% by weight soluble, more preferably no more than about 5% by weight soluble in the gaseous fluid. It is preferable that under the selected processing conditions the solid or semi-solid material is essentially completely insoluble in the gaseous fluid.

By the term "Mode 1" is meant a process according to the present invention using steps (a)(1) and (b)(1) described above wherein a solid or semi-solid material is precipitated out of a gaseous fluid solution.

By the term "Mode 2" is meant a process according to the present invention using steps (a)(2) and (b)(2) described above wherein a solid or semi-solid material is precipitated out of a liquid solution.

In a preferred embodiment of this invention, the supercritical or organic solution is introduced as a spray or a jet directly into a mixed bed of a carrier material, e.g., a drug substance or a carrier material such as lactose, starch or dicalcium phosphate. The orifice producing the spray or jet is located within or close to the bed of carrier particles so that it rapidly contacts the carrier particles. Although not required, mechanical mixing of the carrier material is preferred because it causes the spray to continuously come in contact with different carrier particles, thereby uniformly distributing the precipitated solute throughout the mixed powder and minimizing contact among solute particles. Mechanical mixing also imparts shear to the particles which aids in spreading the spray droplets or formed particles across the surface of the carrier material.

In another preferred embodiment of the present invention wherein a solute material is precipitated from a liquid solution (herein referred to as "Mode 2"), the carrier material is mechanically mixed during the process. Agglomeration may be reduced by mechanical stirring and blending with carrier material which imparts some shear that serves to de-agglomerate particles and causes higher mass transfer rates of the liquid solvent to the fluid phase which reduces contact time among wet particles. Applicants have unexpectedly discovered that powders of carrier material with good flow, handling and compression properties can be used to trap solute material precipitated (e.g. recrystallized) using SCFs to produce powders with similarly good properties. The ability of carrier material to retain recrystallized material can overcome major difficulties with SCF processing. Because carrier particles in a mixed bed are in close proximity to each other, precipitation is believed to occur close to or on the carrier particles; the probability of precipitated microparticles and nanoparticles adhering to carrier particles is enhanced and the probability of adhesion to other like-particles is reduced; the recrystallized particles rapidly interact with carrier particles and are not carried away by continuously flowing SCF that would entrain such small particles. This results in high drug recovery. The carrier can therefore act as a medium for adhesion of recrystallized particles, as a medium for filtering recrystallized particles out of the fluid mixture and as a medium for dispersing the recrystallized particles. A high throughput is also achieved because the need for a flow restrictive filter is alleviated since most fine microparticles and nanoparticles are retained in the carrier material. Another particular advantage of the process of the present invention is that it can be used to process either solid or semi-solid solute material from either liquid or supercritical solutions. Solid and semi-solid solute particles are rapidly dispersed within carrier material as they are formed thereby minimizing their agglomeration with like solute particles. It should be noted that although mechanical mixing introduces shear to facilitate solute distribution and deagglomeration, agglomeration may also be enhanced if desired by controlling processing parameters such as the rate of addition of a binder solution into the pressurized gaseous fluid. Therefore, the process may be used to cause adherance of recrystallized particles to carrier particles, granulate such particles, or improve their flow properties.

I. Mode 1

Steps (a)(1) and (b)(1) of the present inventive method are analogous to the RESS technique of precipitating gaseous fluid (e.g. SCF) soluble material from a pressurized gaseous fluid solution by introducing the solution into a region of lower pressure or a region containing an inert gas. Such techniques are described, for example, in the following U.S. Patents, each of which is incorporated herein by reference in its entirety: U.S. Pat. No. 4,582,731 and U.S. Pat. No. 4,734,451. Based on the RESS technique known in the art, one skilled in the art can readily adapt and employ the RESS method to the process of the present invention.

In general, any of the conventional conditions (i.e., temperature, pressure, precipitation vessels, nozzle variations, etc) that are commonly used in the art for the RESS technique can be employed in steps (a)(1) and (b)(1) of the present inventive method. These processing conditions can of course be adjusted by the skilled technician over wide ranges to obtain the desired optimum performance of the inventive method. Preferred conditions are as followed: The pressurized gaseous fluid solution temperature is preferably higher than $T_c$ of the gaseous fluid, more preferably in the range of about 1 to $1.6 \times T_c$; the pressure of the pressurized gaseous fluid solution is preferably higher that $P_c$, more preferably in the range of about 1 to $15 \times P_c$; Pressure and temperature in the particle collection vessel or region are preferably ambient or close to ambient conditions. The gaseous fluid is preferably $CO_2$, nitrous oxide, ethane, ethylene or propane, more preferably $CO_2$. Gaseous fluids may be recycled to the process if desired.

In one preferred embodiment of the present invention, a pressurized gaseous fluid solution of a solute is expanded onto or into a mixed bed of carrier particles in a particle collection vessel held at a lower pressure. The gaseous fluid enters the vessel from a location within the carrier bed, or slightly above the upper surface, or from underneath the carrier particle bed and exits the vessel though an alternate opening at the bottom, side or top of the vessel. The gaseous fluid preferably enters the vessel from a location slightly above the upper surface of the carrier particle bed and exits through an opening at the bottom of the vessel. This will help to ensure that the precipitated particles contact the carrier particles intimately prior to exiting the particle collection vessel. The bed of carrier particles is preferably stirred using one or more rotating mixing devices. Speeds in the range of 0 to 5,000 RPM, preferably 50 to 3,000 RPM, may be used.

II. Mode 2

Steps (a)(2) and (b)(2) of the present inventive method are similar to the SAS and GAS techniques of precipitating gaseous fluid insoluble material from a solution of the material in a liquid solvent (e.g., an organic solvent or a mixture of an organic solvent and water) by either introducing the solution into a region containing a pressurized gaseous fluid in which said liquid solvent is soluble but the dissolved solute is substantially insoluble, or by introducing the solution into a region into which the pressurized gaseous fluid is subsequently added to cause the precipitation of the gaseous fluid insoluble material. Such techniques, including the GAS, SAS, ASES and SEDS variations thereof, are described, for example, in the following U.S. Patents, each of which is incorporated herein by reference in its entirety: U.S. Pat. No. 5,360,478; U.S. Pat. No. 5,389,263; U.S. Pat. No. 4,828,702; U.S. Pat. No. 5,833,891; U.S. Pat. No. 5,874,029; U.S. Pat. No. 5,707,634; U.S. Pat. No. 6,063,910; U.S. Pat. No. 5,851,453; U.S. Pat. No. 6,063,138; U.S. Pat. No. 5,795,594; U.S. Pat. No. 5,770,559 and U.S. Pat. No. 5,803,966. Based on the SAS techniques known in the art, one skilled in the art can readily adapt and employ the SAS method to the process of the present invention.

In general, when practicing Mode 2 of the invention by introducing the solution into a vessel containing a pressurized gaseous fluid any of the conventional conditions (i.e., temperature, pressure, fluid flow rates, precipitation vessels, nozzle variations, etc) that are commonly used in the art for SAS can be employed in steps (a)(2) and (b)(2) of the present inventive method. When practicing Mode 2 of the invention by introducing the solution into a vessel and subsequently adding the pressurized gaseous fluid to the vessel, any of the conventional conditions (i.e., temperature, pressure, fluid flow rate, precipitation vessels, nozzle variations, etc) that are commonly used in the art for GAS can be employed in steps (a)(2) and (b)(2) of the present inventive method. These processing conditions can of course be adjusted by the skilled technician over wide ranges to obtain the desired optimum performance of the inventive method.

Preferred conditions are as follows: The temperature in the precipitation vessel is preferably higher than the critical temperature of the gaseous fluid, more preferably in the range of about 1 to 1.6×$T_c$, and the pressure in the precipitation vessel is preferably higher than the critical pressure of the gaseous fluid, more preferably in the range of about 1 to 15×$P_c$, The ratio of liquid solution flow rate to gaseous fluid flow rate should preferably be in the range of about 0.001 to 0.1, more preferably in the range of about 0.01 to 0.05. Pressure, temperature, gaseous fluid flow rate and liquid solution flow rate should preferably be such that the fluid mixture in the precipitation vessel is homogeneous. The bed of carrier particles is preferably stirred using one or more rotating mixing devices. Speeds in the range of 50 to 3,000 RPM are preferred.

The nozzle through which the liquid solution may be introduced into the precipitation vessel can be, for example, an orifice nozzle, a capillary nozzle, an ultrasonic nozzle, or a coaxial nozzle, e.g. the type employed in a SEDS method, as discussed previously. The liquid solution may alternatively be introduced through a regular flow line or orifice with no spray atomization capability. In one embodiment, the solution may be added very quickly or mixed with the carrier material before vessel closure, pressurization, and flow of the gaseous fluid begins.

The pressurized gaseous fluid is preferably pumped into the vessel from above the upper surface where the carrier powder bed is at rest. The liquid solution is preferably introduced into the vessel from a level below or slightly above the upper surface of the carrier powder bed at rest. Since the liquid is sprayed directly onto or into the powder bed, it is believed that at least some particle formation may take place by SFE of the solvent from droplets of solution on the carrier particles. Specifically, droplets of the liquid solution may make contact with and adhere to the carrier material and precipitation of the solid or semi-solid material would then result from the extraction of the liquid solvent from said droplets into said gaseous fluid. If this does occur, the precipitated particles would be formed from a droplet of solution adhered to the carrier particle and may result in the formation of a thin coating of the precipitated material on the carrier particle; the selection of a good wetting solvent would therefore serve to enhance adhesion and surface distribution of the solute on the carrier particles. In the case where the liquid solution is first added to the carrier prior to pressurization with the gaseous fluid, the gaseous fluid may serve to dissolve in and expand the liquid solution to a level where the solid or semi-solid material is no longer soluble in the mixture of gaseous fluid-liquid solvent, thereby effecting precipitation.

Depending on operating conditions of pressure, temperature, fluid flow rates and stirring intensity, particles precipitated from the droplets can form either particles loosely adhered to carrier particles, a coating on carrier particles or a granulation, or mixtures thereof. For coating of carrier particles, the need for wetting the surface of the carrier particles in order to obtain a strong coating can therefore be satisfied with this invention. A change in the location of the opening or orifice producing the spray can be used to change the characteristics of the resulting powder. The closer the orifice is to the powder bed, the wetter the carrier particles, and the greater the potential for coating or granulating the powder mixture. This method of the invention is ideally suited for rapid granulation of pharmaceutical formulations. In-situ particle formation and granulation or coating can eliminate several downstream handling and processing steps and can therefore reduce health risks and production costs.

III. Retention and Dispersion of Precipitated Particles in the Carrier

In steps (c) and (d) of the inventive method, the introduced solution and resulting precipitated particles produced via Mode 1 (steps (a)(1) and (b)(1)) or Mode 2 (steps (a)(2) and (b)(2)) discussed previously are directed onto or into the carrier material bed such that there is retention of the precipitated particles in the carrier material. This is accomplished by introducing the gaseous fluid solution or liquid solvent solution of (a)(1) or (a)(2) into the appropriate region as specified in steps (b)(1) or (b)(2), and onto or into the mixed bed of carrier material such that at least some of the particles precipitating out of the gaseous fluid or liquid solvent solution are retained by the carrier material. Depending on the processing parameters, this can result in the production of a blend of the solid or semi-solid precipitated material with carrier material, a granulation of the solid or semi-solid precipitated material with carrier material, or carrier material partially or fully coated with carrier material, or mixtures thereof.

In either Mode 1 or Mode 2, the precipitation vessel can be partially or fully loaded with carrier material. The process conditions within the precipitation vessel itself (e.g., temperature, pressure, fluid flow rates) can fall within a wide range and can be readily adjusted by the skilled technician to obtain the desired optimum performance of the inventive method. When employing Mode 1, preferred processing conditions are as follows: Pressure and temperature in the precipitation vessel or region are preferably ambient or close to ambient conditions. The bed of carrier particles is preferably stirred using one or more rotating mixing devices. Speeds in the range of 0 to 5,000 RPM, e.g., 50 to 3,000 RPM, are preferred. When Mode 2 is employed, preferred processing conditions are: The temperature in the precipitation vessel or region is preferably higher than the critical temperature of the gaseous fluid, more preferably in the range of about 1 to 1.6×$T_c$, and pressure is preferably higher than the critical pressure of the gaseous fluid, more preferably in the range of about 1 to 15×$P_c$. The ratio of liquid solution flow rate to gaseous fluid flow rate should preferably be in the range of about 0.001 to 0.1, more preferably in the range of about 0.01 to 0.05. Pressure, temperature, gaseous fluid flow rate and liquid solution flow rate should preferably be such that the fluid mixture in the vessel is homogeneous.

In one preferred embodiment, the carrier material bed is maintained in a mixed state (e.g. by continuous stirring, agitating, or mixing by any other means) during the precipitation of the solid or semi-solid material to disperse it throughout the bed of carrier material. Specifically, in this embodiment the carrier bed is maintained in a mixed state at least during steps (c) and (d) of the inventive method. Stirring of a carrier material powder can be accomplished easily, irrespective of particle size distribution and its change throughout the process. In this preferred embodiment, because of the closeness of the spray to the carrier material bed, the stirring which continuously recirculates carrier powder particles through the spray, and the closeness of carrier particles to each other, recrystallized solute particles are rapidly incorporated into the bed of carrier particles preferably before any substantial agglomeration takes place among the solute particles. Solute-solute interaction, which leads to agglomeration, is thereby minimized. In Mode 2, for example, vigorous stirring can alleviate the need for fine atomized sprays of organic solutions in order to produce fine microparticles and nanoparticles of precipitated material. Mechanical stirring may be effected using any of a number of mixing device designs, including pitched, curved or flat blade turbines, anchors, impellers, propellers, dispersers, homogenizers, and helical ribbons. The bed of carrier particles is preferably stirred using one or more rotating mixing devices. Speeds in the range of 50 to 3,000 RPM are preferred.

As discussed previously, the distance between the mixed bed of carrier material and the opening or orifice through which the gaseous fluid solution or liquid solution is introduced into the precipitation chamber will affect the characteristics and quality of the mixture obtained. One skilled in the art can easily adjust this distance as well as pressure, temperature and liquid and fluid flow rates to obtain the desired product, be it a blend, granulation or coated carrier material or mixtures thereof, while preferably preventing substantial agglomeration among the precipitated particles. In a preferred embodiment, for example, the precipitated particles are directed onto or into the mixed bed of carrier material by introducing the gaseous fluid solution or the liquid solution through an opening located above and close to the surface of the bed of mixed carrier material or through an opening located within the bed of mixed carrier material.

In another preferred embodiment, the precipitated particles are directed onto or into the mixed bed of carrier material through an opening located at a distance of at least about 0 to 12 inches, preferably at least about 2 inches, from the surface of the bed of mixed carrier material or through an opening located within the bed of mixed carrier material. The surface of the bed may increase over time as more solid or semi-solid precipitated material, for example, drug, coating, and/or binder material is added to the carrier bed.

As discussed previously, by adjusting the processing parameters, the final product of this inventive method can either be a blend of solid or semi-solid material particles with carrier material, a granulation of solid or semi-solid material particles with carrier material, or carrier material partially or fully coated with solid or semi-solid material particles. The blends, granulations, partially or fully coated carrier materials, or mixtures thereof, produced by the methods according to the present invention can be processed into various pharmaceutical formulations and dosage forms, such as tablets and capsules, by conventional techniques. In the case of a blend, the product can be a uniform or non-uniform mixture of carrier material, discrete particles of solid or semi-solid material, and carrier material having solid or semi-solid material loosely adhered thereto. In the case of a coating technique, the inventive method can be repeated one or more times on the initially coated carrier material using the same or different coating materials. Specifically, a coated carrier material produced in step (d) can be further coated by performing a coating method of the present invention one or more times on said coated carrier material, wherein the solid or semi-solid material used in the initial and subsequent coating methods may be the same or different during each coating method.

For example, as discussed above the carrier material may be initially coated with a drug substance followed by coating with an encapsulating material and the entire process can be repeated to increase drug loading. The drug substance can also be coated with a moisture, light or gas protecting material or a diffusion barrier material, or dissolution or dispersion enhancing material, or combinations thereof in different coating layers. A wide number of variations and applications of this coating technique are possible.

In the case of granulation, a binder such as PVP may be present either in admixture with a drug substance in the liquid or pressurized gaseous fluid solution or in admixture within the carrier powder bed.

In either Mode 1 or Mode 2 of the invention, the gaseous fluid can flow out of the vessel after contact with the powder bed. It is preferred that the gaseous fluid flow through a large fraction of the powder bed prior to exiting the vessel through a filter sized small enough to retain at least the carrier particles. It is therefore preferred that the solute-depleted fluid mixture flow out the precipitation vessel through a filter located at the bottom of the carrier bed. This should ensure a high particle retention efficiency and more uniform rate of mass transfer of solvent into the gaseous fluid in the case of Mode 2. In this preferred mode, depending of the location of the spray, stirring may be optional during the process, especially in Mode 1 of the invention. Stirring may be required if a uniform distribution of recrystallized material in the carrier material is desired. This preferred mode is made possible by the relatively low viscosity and high diffusivity of gaseous fluids and gases and the high particle retention efficiency of the carrier material.

In Mode 2, it is preferred that after precipitation of the solute from the liquid solution, the liquid solvent-gaseous fluid mixture flows out of the precipitation vessel and is then expanded at a reduced pressure level to separate the gaseous fluid from the liquid solvent. The liquid solvent can be recovered in a cold trap and the gaseous fluid vented or recycled into the process.

FIG. 1 depicts flow diagrams showing two specific embodiments of Modes 1 and 2 of the present inventive method.

A variety of solid or semi-solid materials, gaseous fluids, liquid solvents, and carrier materials can be employed in the present inventive method to produce a variety of types of products.

For example, the solid or semi-solid material that is precipitated can be selected from physiologically active materials, such as a chemical pharmaceuticals, and agricultural materials such as herbicides and fertilizers. The solid or semi-solid material may also be an industrial chemical, foodstuff, fine chemical, cosmetic chemical, photographic chemical, dye, paint, polymer, an encapsulating material, a moisture protection material, a light protection material, a gas protection material, a diffusion barrier material or a dissolution or dispersion enhancing material. In a preferred embodiment the solid or semisolid material is a physiologically active material. Of course, mixtures of different solid or semi-solid materials are contemplated and may be processed according to the present invention.

In preferred embodiments, the physiologically active material can be selected from Ipratropium bromide, tiotropium bromide, oxytropium bromide, tipranavir, albuterol, albuterol sulfate, clenbuterol, fenoterol, beclomethasone diproprionate, insulin, amino acids, analgesics, anti-cancer agents, antimicrobial agents, antiviral agents, antifungals, antibiotics, nucleotides, amino acids, peptides, proteins, immune suppressants, thrombolytics, anticoagulants, central nervous system stimulants, decongestants, diuretic vasodilators, antipsychotics, neurotransmitters, sedatives, hormones, anesthetics, anti-inflammatories, antioxidants, antihistamines, vitamins, minerals and other physiologically active materials known to the art; the encapsulating material can be selected from the above physiologically active materials, gels, waxes, polymers, and fatty acids; the moisture protection material, gas protection material and diffusion barrier material can each be selected from lecithin and polymers such as polyethylene glycol, PVP, and polyvinyl alcohol; and the light protection material can be selected from polymers and titanium dioxide. Dissolution or dispersion enhancers can be selected from surfactants (e.g., tween), or wetting agents (e.g., sls, sds), solubilizing agents, dispersing agents, carrier surface modification materials such as polymers that promote adhesion (PVP, PVA, cellulose), or silicon dioxide, etc.

The precipitated particles of solid or semi-solid material that are produced in the inventive process may comprise microparticles or nanoparticles of solid or semi-solid material, or mixtures thereof. The process is particularly suited to the efficient retention of such small particles in the carrier material.

The gaseous fluid employed in the inventive method includes, for example, any gaseous fluid that is commonly employed in conventional supercritical fluid processes such as SFE, RESS and SAS. Examples of suitable gaseous fluids include carbon dioxide, nitrous oxide, trifluoromethane, ethane, ethylene, propane, sulfur hexafluoride, propylene, butane, isobutane, pentane, and mixtures thereof.

The liquid solvent that may be employed in the inventive method includes, for example, water or any organic liquid solvent that may be employed in conventional SAS processes. Examples of organic solvents that may be used include aliphatic alcohols, such as ethanol, methanol, propanol and isopropanol, acetone, dichloromethane, ethyl acetate, dimethyl sulfoxide, polymers, surface wetting enhancer(s) such as surfactants, and mixtures thereof. Water may also be present in admixture with any of the above organic solvents.

The carrier material used in the inventive method can be selected from any pharmaceutically acceptable carrier, adjuvant or excipient, or a physiologically active material, or mixtures thereof. Preferred examples of pharmaceutically acceptable carriers, adjuvant or excipient that can be used include lactose, including hydrated forms thereof, dextrose, sucrose, starch, polyethylene glycol, PVP, polyvinyl alcohol, lecithin, microcrystalline cellulose, hydroxypropyl methyl cellulose, calcium carbonate, dicalcium phosphate, calcium triphosphate, magnesium carbonate and sodium chloride. Preferred examples of physiologically active materials that can be used as carrier materials include Ipratropium bromide (I.B.), tiotropium bromide, oxytropium bromide, albuterol, albuterol sulfate, clenbuterol, fenoterol, beclomethasone diproprionate, insulin, amino acids, analgesics, anti-cancer agents, antimicrobial agents, antiviral agents, antifungals, antibiotics, nucleotides, amino acids, peptides, proteins, immune suppressants, thrombolytics, anticoagulants, central nervous system stimulants, decongestants, diuretic vasodilators, antipsychotics, neurotransmitters, sedatives, hormones, anesthetics, anti-inflammatories antioxidants, antihistamines, vitamins, minerals. The carrier material can also take a variety of forms depending on the desired product such as, for example, a powder, granulated powder, tablets, capsules or caplets. When the carrier material is a powder it can take the form of microparticles or nanoparticles of carrier material, or mixtures thereof.

In one preferred embodiment, the carrier material is a powder comprising microparticles and/or nanoparticles of pharmaceutically acceptable carrier, adjuvant or excipient, or microparticles and/or nanoparticles of a physiologically active material, or mixtures thereof.

Another specific embodiment of Mode 1 of the inventive process is directed to a method for particle precipitation, retention and dispersion in carrier material comprising:

(a) dissolving a solid or semi-solid physiologically active material in a pressurized gaseous fluid, thereby forming a solution comprising pressurized gaseous fluid solvent and dissolved physiologically active material;

(b) precipitating microparticles and/or nanoparticles of the physiologically active material out of the gaseous fluid solution produced in step (a) by introducing the solution through an orifice into a lower pressure region or into a region containing an inert gas;

(c) directing the introduced solution and resulting microparticles and/or nanoparticles produced in step (b) onto or into a mixed bed of powdered carrier material, said powdered carrier material comprising microparticles and/or nanoparticles of a pharmaceutically acceptable carrier, adjuvant or excipient; and (d) retaining at least some of the microparticles and/or nanoparticles produced in step (b) in the powdered carrier material to produce a blend of the physiologically active material particles and carrier material, a granulation of the physiologically active material particles with carrier material, carrier material partially or fully coated with the physiologically active material, or mixtures thereof.

Additional embodiments are directed to the Mode 1 method set forth above wherein: the pressurized gaseous fluid is carbon dioxide; the region into which the gaseous fluid solution is introduced is a lower pressure region; the orifice is located above the upper surface of the mixed bed of carrier material when the mixed bed is at rest or within the mixed bed when the mixed bed is at rest; the carrier material is lactose; the mixed bed of carrier material is maintained in a mixed state during steps (c) and (d), e.g, by mixing at a speed of about 300 to 1,000 RPM; and/or the product of step (d) is at least some powdered carrier material partially or fully coated with the physiologically active material.

Another specific embodiment of Mode 2 of the inventive process is directed to a method for particle precipitation, retention and dispersion in carrier material comprising:

(a) dissolving a solid or semi-solid physiologically active material in a liquid solvent, thereby forming a solution comprising a liquid solvent and a dissolved physiologically active material (b) precipitating microparticles and/or nanoparticles of the physiologically active material out of the liquid solution produced in step (a) by introducing the solution through an orifice into either: (1) a region containing pressurized gaseous fluid in which said liquid solvent is substantially soluble but said physiologically active material is substantially insoluble, or (2) a region into which said pressurized gaseous fluid is subsequently introduced to cause the solubilization of the liquid solvent into the pressurized gaseous fluid and the precipitation of said microparticles and/or nanoparticles;

(c) directing the introduced solution and resulting microparticles and/or nanoparticles produced in step (b) onto or into a mixed bed of powdered carrier material, said powdered carrier material comprising microparticles and/or nanoparticles of a pharmaceutically acceptable carrier, adjuvant or excipient; and (d) retaining at least some of the microparticles and/or nanoparticles produced in step (b) in the powdered carrier material to produce a blend of the physiologically active material particles and carrier material, a granulation of the physiologically active material particles with carrier material, carrier material partially or fully coated with physiologically active material, or mixtures thereof.

Additional embodiments are directed to the Mode 2 method set forth above wherein: the liquid solvent is a liquid organic solvent, for example, an aliphatic alcohol solvent; the gaseous fluid is carbon dioxide; the liquid solution is sprayed through an orifice into a region containing a pressurized gaseous fluid, wherein the orifice is located above the upper surface of the mixed bed of carrier material when the mixed bed is at rest or is located within the mixed bed when the mixed bed is at rest; the mixed bed of carrier material is maintained in a mixed state during steps (c) and (d); and/or the product of step (d) is at least some powdered carrier material partially or fully coated with the physiologically active material.

A further embodiment is directed to the Mode 2 methods set forth above wherein during steps (b) and (c) droplets of the liquid solution make contact with the powdered carrier material and precipitation of the physiologically active material results from the extraction of the liquid solvent from said droplets into the pressurized gaseous fluid.

Further additional embodiments are directed to the Mode 2 processes set forth above, wherein a solid or semi-solid physiologically active material and a solid or semi-solid binder material are both dissolved in the liquid solution in step (a); the liquid solvent is methanol or ethanol; the carrier material is lactose; and/or the mixed bed of carrier material is maintained in a mixed state by mixing at a speed of about 20 to 1,000 RPM, preferably about 300 to 1,000 RPM The following examples set forth techniques demonstrating various aspects of the present invention. It is to be understood, however, that these examples are presented by way of illustration only and that nothing therein should be taken as a limitation upon the overall scope of the present invention.

The objective of these examples is to demonstrate that the present invention can be used to deposit solutes from organic solutions or gaseous fluids or mixtures thereof to form blends of a solute material on a carrier wherein the solute is distributed mostly on the carrier as either discrete particles, a coating around the carrier particles, or a mixture of a coating and discrete particles.

EXAMPLES

Example 1

Recrystallization of a Drug Substance from Supercritical $CO_2$ and Coating of Polymeric Micro-beads Five (5) grams of a drug substance was mixed with an inert material (diatomaceous earth) and charged into a 1 liter vessel. Supercritical $CO_2$ at 80° C. and 310 bar was then used to extract and solubilize the drug substance. The drug-laden effluent $CO_2$ stream was then expanded to a lower pressure through a 75 $\mu$m orifice nozzle located in a 300 mL mixing vessel containing 25 grams of a white powder that consists of polystyrene divinyl benzene beads with a particle size in the range of 40–80 $\mu$m. The powder was mixed at 1,000 RPM using two 4-blade pitched radial impellers attached to the drive shaft. The bottom impeller was located near the bottom of the vessel. The nozzle lip was set close to the top of the powder bed so that the drug substance precipitated as microparticles and nanoparticles and rapidly mixed with the powder. Mixing vessel temperature and pressure were 40–50° C. and up to 1,000 psig. Effluent $CO_2$ passed through a 60 $\mu$m filter frit and was then vented.

The treated powder bore a yellowish, evenly distributed color, suggesting that the drug was uniformly distributed throughout the powder. FIG. 2 shows a light microscopy image of a bead subjected to supercritical $CO_2$ at 50° C. and 1,000 psig. Polaroid software version 1.1 was used to view images on the microscope (Olympus BH2 Polarized Light Microscope and Polaroid DMC 1e). The bead appears to be spherical and is not damaged by high-pressure $CO_2$. FIG. 3 shows a light microscopy image of a bead which was treated according to the invention. The surface appears to be covered with extraneous material and a coating appears to be deposited on its surface. Drug material appeared to be adhered to the beads.

Example 2

Recrystallization of a Drug Substance from Supercritical $CO_2$ and Coating of Lactose Monohydrate In this Example, the beads used in the above example were replaced with lactose monohydrate, a widely used excipient material in tablet formulations. The processed powder contained about 10% drug, bore a yellowish color and appeared to have flow properties similar to those of unprocessed lactose. Light Microcopy (or bright field microscopy) and scanning electron microscopy did not provide evidence on the location of the drug substance within the processed powder. Because the drug substance is brightly fluorescent and lactose is not fluorescent, fluorescence microscopy was used to demonstrate that drug particles are fully associated with lactose particles.

Samples were prepared from processed dry powders by sprinkling a small amount of powder onto a glass microscope slide, adding 3 drops of non-fluorescent immersion oil and covering with a number 1.5 glass cover slip. Preparations were kept for less than one day at room temperature and were protected from light except when being examined in the microscope.

The microscope was a Nikon Microphot with a band pass filter tuned for fluorescence in Isothiocyanate emission. Samples were examined in bright field (tungsten) and UV illumination (high pressure mercury vapor lamp), with 20×, 40× and 60×objectives. Magnification calibration was performed with a Don Santo stage micrometer (1 mm divided into 10 micrometer intervals). Images were captured with a SVMicro digital camera.

FIG. 4 shows in bright field illumination a group of lactose particles treated with the drug substance. A typical appearance of a group of particles viewed in bright field illumination is observed. FIG. 5 shows the same field illuminated with UV light. Each particle is fluorescent indicating that each lactose particle is associated with the drug substance. This technique can therefore be used to produce intimately and uniformly mixed powders.

Because the depth of focus is so shallow, it was possible to get images that are ‘optical sections” through particles using a high numerical aperture objective. These images show that the fluorescent drug is selectively located on the surfaces of the lactose particles, almost as a “shell” or a coating. Very little, if any, drug was found within the lactose particles.

Dissolution of the above drug-lactose mixture was then conducted using the standard stirred basket method and compared to the dissolution of a conventional physical powder mixture of drug-lactose using the same dissolution method. The two drug-lactose mixtures that were analyzed had the same drug/lactose ratio. The dissolution profiles, see FIG. 6, show that supercritical fluid-processed material exhibits faster dissolution, with sometimes as much as double the amount drug release per time period.

Example 3

Precipitation of a Drug Substance from a Sprayed Organic Solution and Blending it into and/or Coating it onto Lactose Particles with the Nozzle Above the Bed In this example, a mass of 25 grams of lactose (approximate size: 99% less than 63 $\mu$m) was charged into a 300 mL vessel immersed in an isothermal (50° C.) water bath. The vessel was closed, mixing was started at 1000 rpm and $CO_2$ flow through the vessel was then established. Upon reaching the desired pressure of 1,500 psig, about 95 mL of a solution of 25 mg/mL of a drug substance in methanol was sprayed through a 75 μm nozzle for about 1 hour at 1.5 mL/min. The nozzle tip was set at about 4 inches above the powder bed at rest. The solution rapidly mixed with supercritical $CO_2$ causing the $CO_2$ insoluble drug to rapidly crystallize and blend within the bed. Following addition of the solution, drying was allowed to take place for about 2 hours. Effluent solvent-supercritical $CO_2$ mixture passed through a 60 μm filter and then was expanded down to atmospheric level. Solvent was recovered in a cold trap and gaseous $CO_2$ was vented to the atmosphere. Effluent near-atmospheric pressure $CO_2$ flow rate was about 45 standard liters per minute throughout this period.

Example 4

Precipitation of a Drug Substance from a Sprayed Organic Solution and Blending it into and/or Coating it onto Lactose Particles with the Nozzle in or Near the Bed This example was a repeat of Example 3 except the nozzle was lowered to about 1 inch above the powder bed at rest. As expected, during stirring the bed covered the nozzle.

Figure 7A:
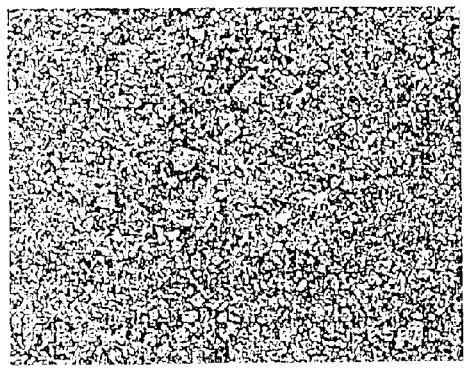
FIGS. 7A to 7C are SEM (Scanning Electron Microscope) photomicrographs of excipient lactose before processing in accordance with the invention.
Figure 7B:
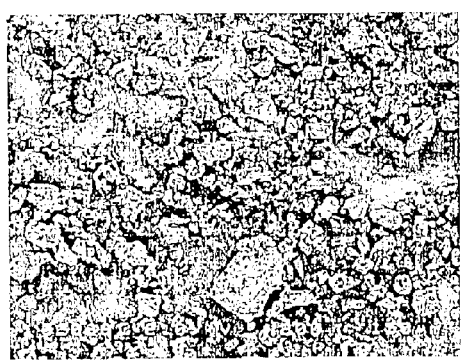
Figure 7C:
Figure 8A:
FIGS. 8A to 8C are SEM photomicrographs of drug solute precipitated by processing out of solution without using a carrier material and without mixing.
Figure 8B:
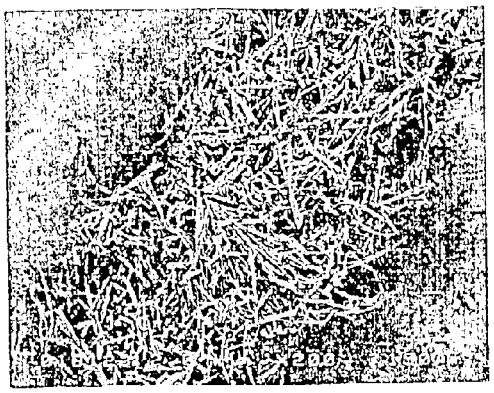
Figure 8C:
Figure 9A:
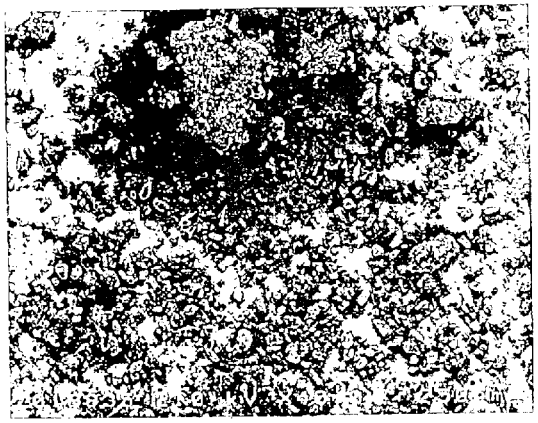
FIGS. 9A to 9C are SEM photomicrographs of a drug/lactose mixture obtained using a method of the present invention wherein the drug substance was precipitated from a sprayed organic solution and blended into and/or coated onto the lactose. In this example, the organic solution was sprayed through a nozzle at a distance of about 1 inch above the lactose powder bed.
Figure 9B:
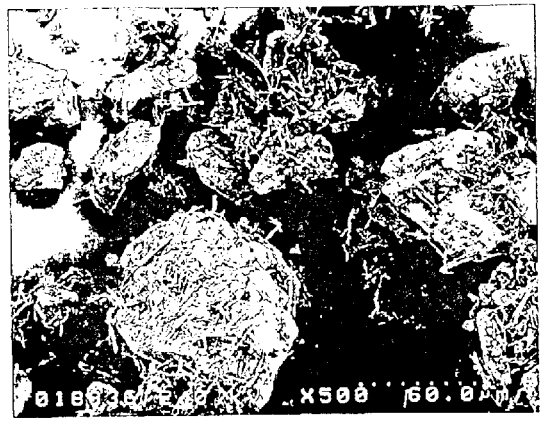
Figure 9C:

No differences could be seen between the two resulting products of Examples 3 and 4. The resulting product theoretically contained 10% drug load, visually appeared to be granular, and had acceptable flow which was not characteristic of the carrier starting material before processing. No blinding of the filter was noted, indicating the lactose was very efficient at trapping the solute. FIGS. 7A to 7C show SEM photomicrographs of excipient lactose before processing (FIG. 7A is at 40× magnification; FIG. 7B is at 200× magnification; and FIG. 7C is at 5,000× magnification). FIGS. 8A to 8C show SEM photomicrographs of the drug solute precipitated by processing out of solution without lactose and stirring (FIG. 8A is at 40× magnification; FIG. 8B is at 200× magnification; and FIG. 8C is at 5,000× magnification). This is similar to non-processed starting material. The drug substance can be seen to crystallize in the shape of acicular, elongated needle like particles. FIGS. 9A to 9C show SEM photomicrographs of the drug-lactose mixture obtained by the process of Example 4 (FIG. 9A is at 40× magnification; FIG. 9B is at 500× magnification; and FIG. 9C is at 5,000× magnification). There appears to be a blend of various sized clusters or granules. The drug appears as discrete particles, as particles adhered to lactose particles, and/or as particles coated onto the lactose

Example 5

Precipitation of a Drug Substance from a Non-sprayed Organic Solution and Blending it into and/ or Coating it onto Lactose Particles In this example, a mass of 25 grams of lactose (approximate size: 99% less than 63 μm) was charged into a 300 mL vessel immersed in an isothermal (50° C.) water bath. A solution of 100 mL containing 25 mg/mL of a drug substance in methanol was added to the carrier in the vessel. The vessel was closed and mixing was started at 1000 rpm. $CO_2$ flow through the vessel was then established. Upon reaching the desired pressure of 1,500 psig, the process was continued for 2 hours. At near-atmospheric pressure $CO_2$ flow rate was about 45 standard liters per minute. Effluent solvent-supercritical $CO_2$ mixture passed through a 60 μm filter and then was expanded down to atmospheric level. Solvent was recovered in a cold trap and gaseous $CO_2$ was vented to the atmosphere. In this case, the gaseous fluid served to dissolve in and expand the organic solution to a level where the drug substance was no longer soluble in the mixture of gaseous fluid-organic solvent.

Example 6

Precipitation of a Drug Substance from a Non-sprayed Organic Solution and Blending into and/or Coating of Lactose Carrier Particles using Reduced Solvent, Increase Pressure, and an Initial Settling Step In this example which is similar to Example 5, a mass of 25 grams of lactose (approximate size: 99% less than 63 μm) was charged into a 300 mL vessel immersed in an isothermal (50° C.) water bath. A solution of 50 mL containing 50 mg/mL of a drug substance in methanol was added to the carrier in the vessel. The vessel was closed, mixing started at 1000 rpm, and $CO_2$ slowly added to the vessel until the desired pressure of 2,000 psig was established. The stirrer speed was then reduced to 20 rpm and crystallization was allowed to take place for 30 minutes prior to resuming the flow of gaseous fluid into the vessel and solvent-gaseous fluid mixture out of the vessel to effect drying of the powder mix. At near-atmospheric pressure $CO_2$ flow rate was about 45 standard liters per minute. Impeller speed was again increased to about 1,000 RPM and the process was continued for 1 hour and 15 minutes. Effluent solvent-supercritical $CO_2$ mixture passed through a 60 μm filter and then was expanded down to atmospheric level. Solvent was recovered in a cold trap and gaseous $CO_2$ was vented to the atmosphere. The gaseous fluid served to dissolve in and expand the organic solution to a level where the drug substance was no longer soluble in the mixture of gaseous fluid-organic solvent.

Figure 10A:
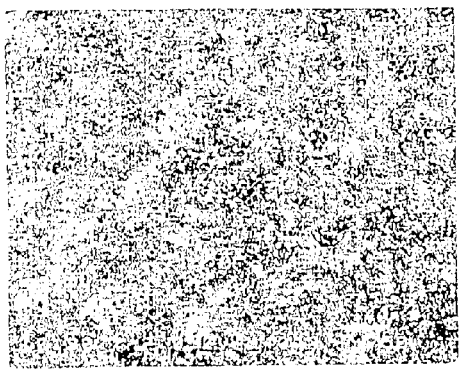
FIGS. 10A to 10C are SEM photomicrographs of a drug/lactose mixture obtained using a method of the present invention wherein the drug substance was precipitated from a non-sprayed organic solution following the introduction of pressurized carbon dioxide, and blended into and/or coated onto the lactose.
Figure 10B:
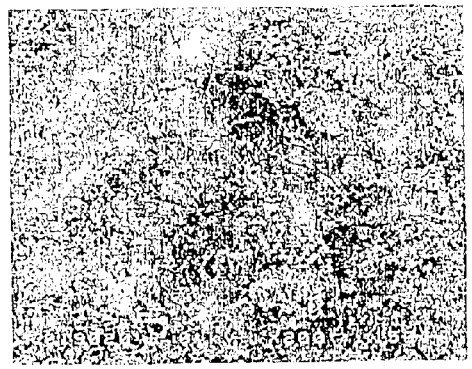
Figure 10C:

The resulting product was very fluffy and about half the density of the starting material. No difference could be detected between this example and the previous Example 5. Although the material was not very dense, it was not adhesive, and had flowability. The filter had only a slight coating of material. FIGS. 10A to 10C show SEM photomicrographs of the drug-lactose mixture obtained by the process of Example 5 (FIG. 10A is at 40× magnification; FIG. 10B is at 200× magnification; and FIG. 10C is at 5,000× magnification). These photomicrographs show that small elongated particles of the drug substance are uniformly distributed throughout the mixture in various sized clusters. Lactose particles appear to be of a size similar to that of drug particles. The exact reason why large lactose particles are no longer observed is not known.

Example 7

Precipitation of a Drug Substance from a Sprayed Organic Solution Containing a Binder and Blending it into and/or Coating it onto Lactose Particles with Good Flow Properties In this example, a mass of 25 grams of lactose (approximate size: 75% less than 100 μm) having excellent flow was charged into a 300 mL vessel immersed in an isothermal (50° C.) water bath. The vessel was closed, mixing was started at 1000 rpm and $CO_2$ flow through the vessel was then established. Upon reaching the desired pressure of 2,000 psig, 200 mL of a solution of 50 mg/mL of a drug substance and 25 mg/mL binder (PVP) in ethanol was sprayed through a 75 μm nozzle for about 2 ¼ hour at 1.5 mL/min. The nozzle tip was set 1 inch above the powder bed. After solution addition the mixture was dried an additional 1 ¼ hours. The solution rapidly mixed with supercritical $CO_2$ causing the $CO_2$-insoluble drug to rapidly crystallize and blend within the bed. Effluent solvent-supercritical $CO_2$ mixture passed through a 60 μm filter and then was expanded down to atmospheric level. Solvent was recovered in a cold trap and gaseous $CO_2$ was vented to the atmosphere. Effluent near-atmospheric pressure $CO_2$ flow rate was about 45 standard liters per minute throughout this period.

Example 8

Precipitation of a Drug Substance from a Sprayed Organic Solution Containing a Binder and Blending it into and/or Coating it onto Lactose Particles with Good Flow Properties at a Medium Rate of Deposition This example is similar to Example 7, except that the spray rate was 3 mL/min. The 200 mL of a solution addition was complete in about 1 ¼ hours. The mixture was dried for an additional 1 ¼ hours.

Example 9

Precipitation of a Drug Substance from a Sprayed Organic Solution Containing a Binder and Blending it into and/or Coating it onto Lactose Particles with Good Flow Properties at a High Rate of Deposition This example is similar to Example 7, except that the stirrer speed was reduced throughout the run to 300 rpm, and the spray rate was 5 mL/min. The 200 mL of a solution addition was complete in about 45 minutes. The mixture was dried for an additional 1 ¼ hours.

Figure 11:
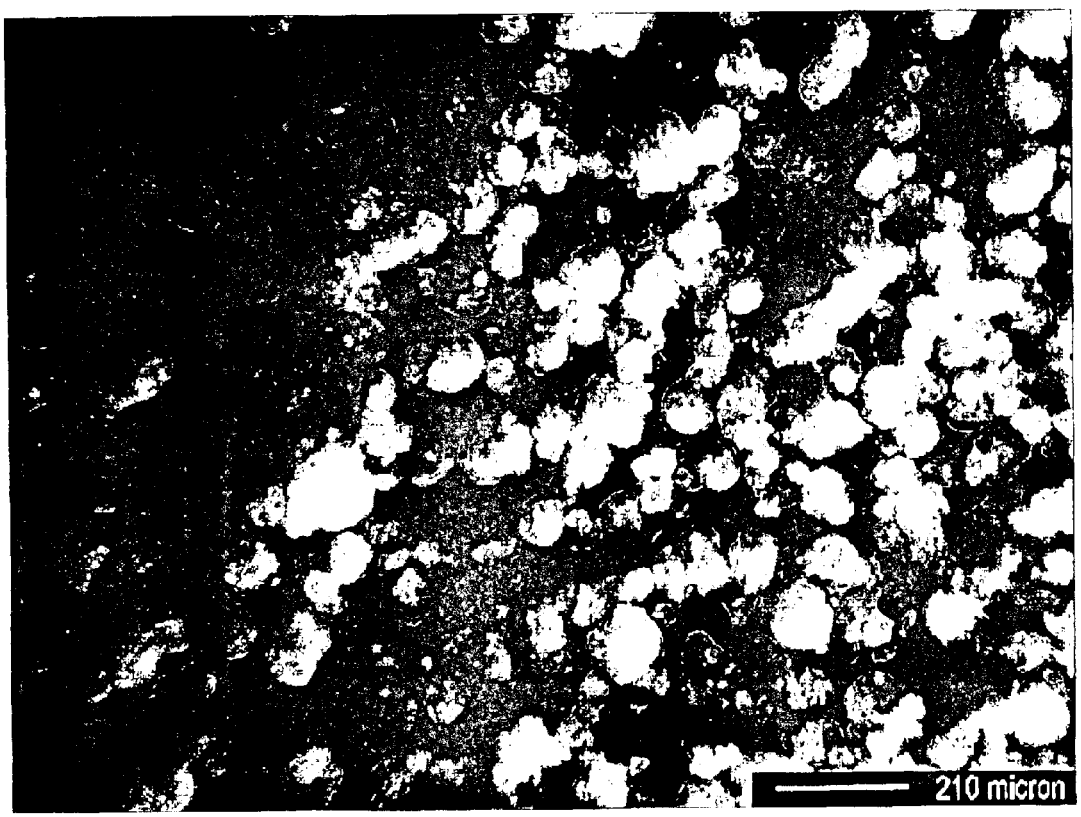
FIG. 11 is a photomicrograph of lactose before processing in accordance with the invention.
Figure 12:
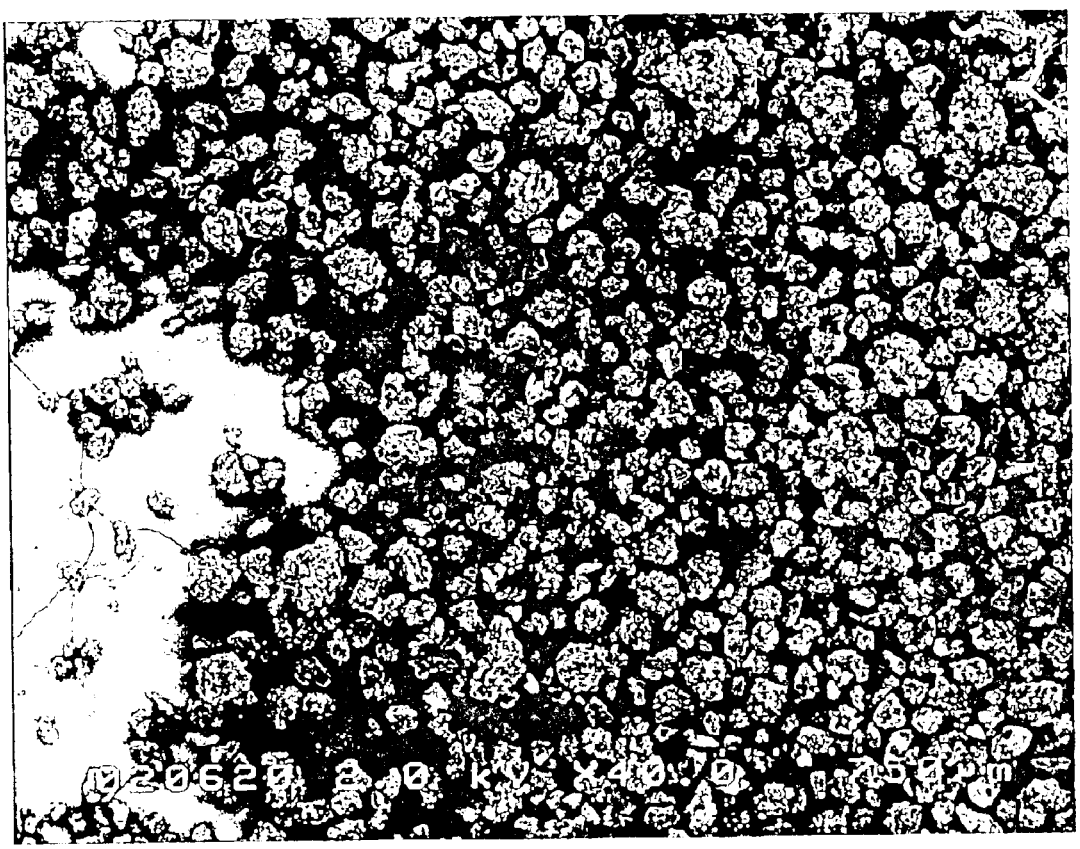
FIGS. 12 to 15 are SEM photomicrographs of a drug/binder/lactose mixture obtained using a method of the present invention wherein the drug substance and binder were precipitated from a sprayed organic solution and blended into and/or coated onto the lactose. In this example, the organic solution was sprayed at a rate of 1.5 mL min through a nozzle located 1 inch above the lactose powder bed, and mixing was at 1000 rpm.
Figure 13:
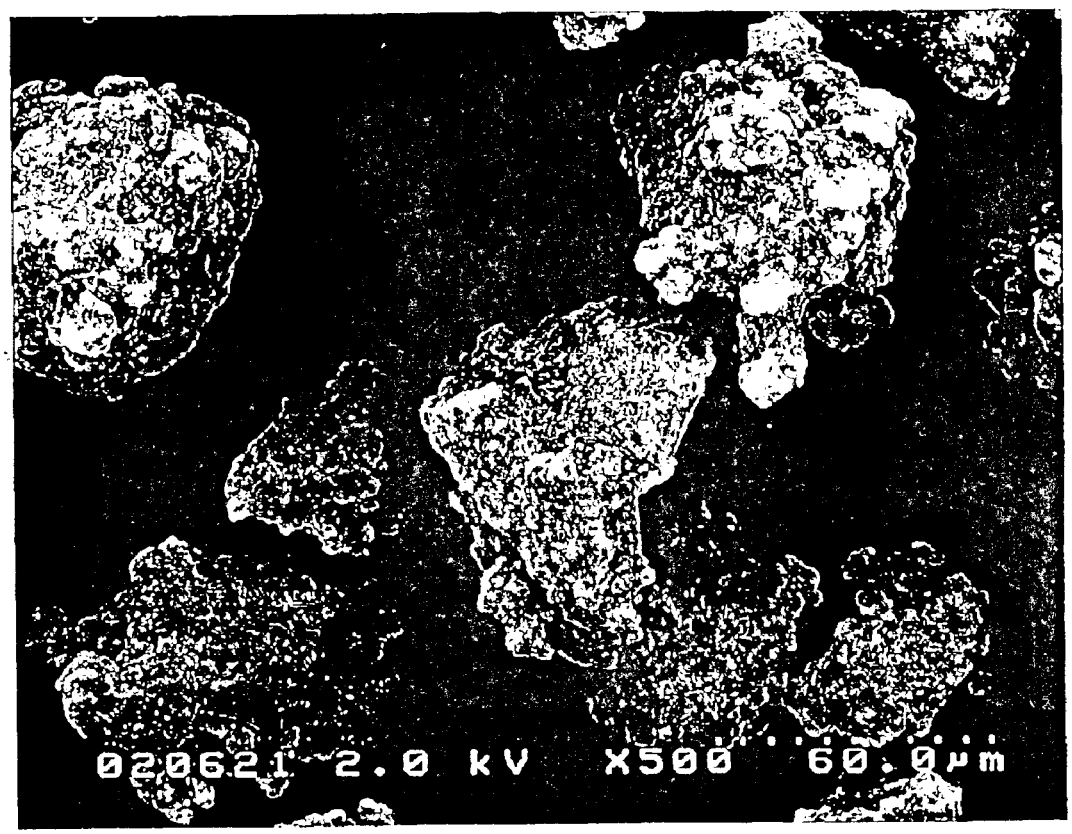
Figure 14:
Figure 15:
Figure 16:
FIG. 16 is a SEM photomicrograph of a drug/binder/lactose mixture obtained using a method of the present invention wherein the drug substance and binder were precipitated from a sprayed organic solution and blended into and/or coated onto the lactose. In this example, the organic solution was sprayed at a rate of 3 mL min through a nozzle located 1 inch above the lactose powder bed, and mixing was at 1000 rpm.
Figure 17:
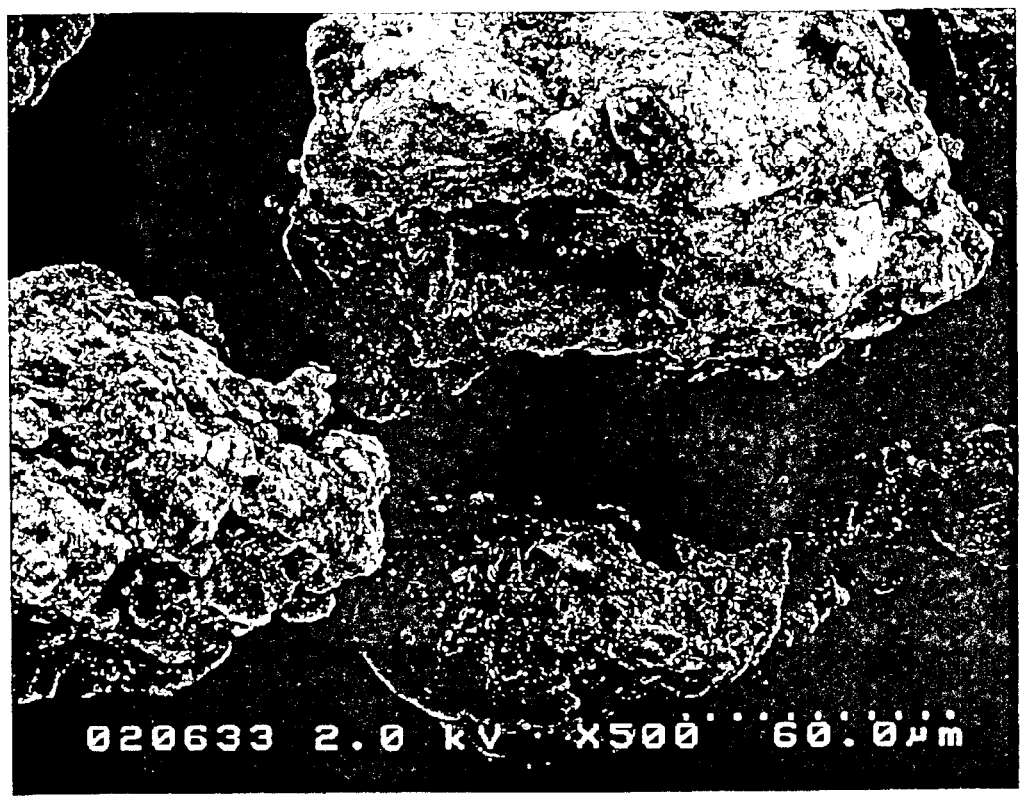
FIGS. 17 to 19 are SEM photomicrographs of a drug/binder/lactose mixture obtained using a method of the present invention wherein the drug substance and binder were precipitated from a sprayed organic solution and blended into and/or coated onto the lactose. In this example, the organic solution was sprayed at a rate of 5 mL min through a nozzle located 1 inch above the lactose powder bed, and mixing was at 300 rpm.
Figure 18:
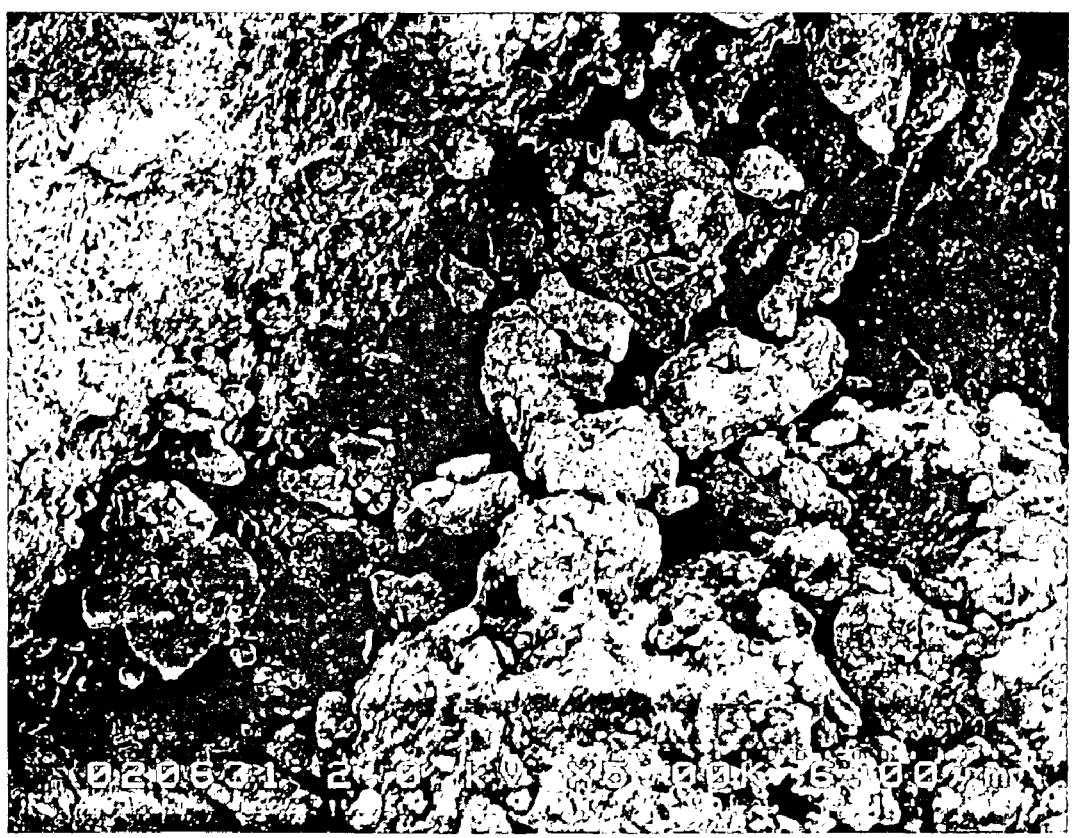
Figure 19:

The resulting products of these last three Examples, 7, 8, and 9, were very free flowing and granular. The dried blend was theoretically 25% drug, 12.5% binder, and 62.5% lactose. The granule size visually appeared larger as the spray rate increased. This is what normally occurs in the process of granulation where powders and a binder are mixed. FIG. 11 is a photomicrograph of the lactose starting material. The uniformly spherical shape and size that promotes good flow is obvious. FIGS. 12–19, are SEM photomicrographs of the granulation products of Examples 7 to 9. FIGS. 12–15 are of Example 7. FIG. 12 (40×) shows that the lactose is uniformly coated and minor granulation or agglomeration of the lactose has taken place. FIGS. 13 (500×) and 14 (2,000×) show that the deposition has taken place as both elongated particles and as droplets of binder and drug materials, which after extraction of the solvent left fused masses of solid. The droplets, sometimes as clusters, also contain lactose and drug fragments. FIG. 15 (5,000×) shows that the precipitated microparticles and/or nanoparticles are a porous deposition with various degrees of binder material present. In FIG. 16 (5,000×) of Example 8, (medium, 3 mL/minute spray rate), more coating and smaller less elongated particles are visible. In FIGS. 17–19 of Example 9 (FIG. 17=500×; FIG. 18=5,000×; FIG. 19=10,000×), a high spray rate has produced granules of the lactose starting material, drug, and binder. These figures show very few individual particles of drug, with drug being fused or coprecipitated with the binder forming a solid or semisolid material deposition onto and between the carrier substrate, lactose.

Figure 20:
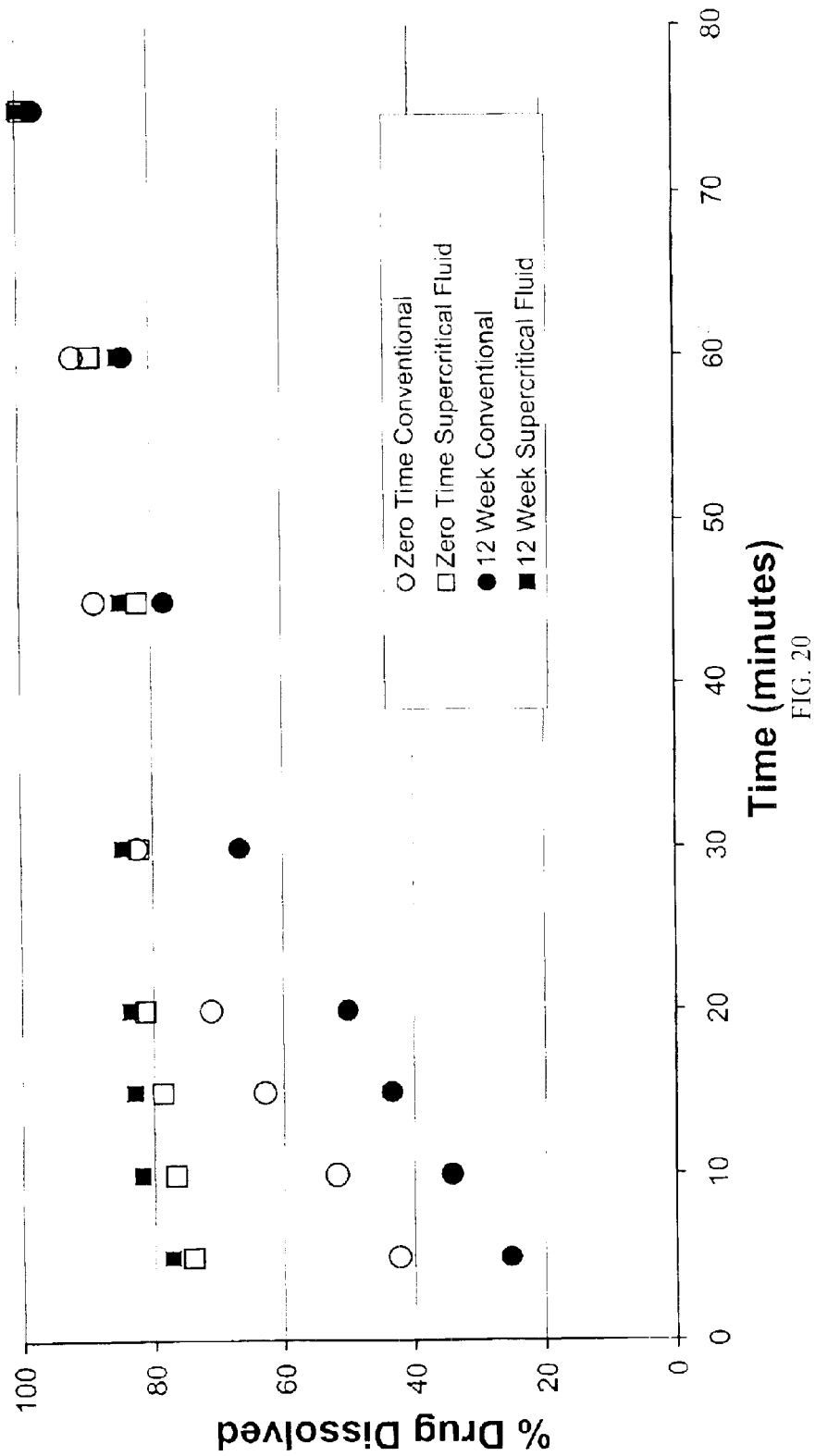
FIG. 20 is a graph showing the dissolution profiles of tablets prepared using a drug-lactose mixture obtained according to a method of the present invention as compared to conventionally processed tablets at time zero and at 12 weeks under standard storage conditions of 40° C. and 75% RH.
Figure 21:
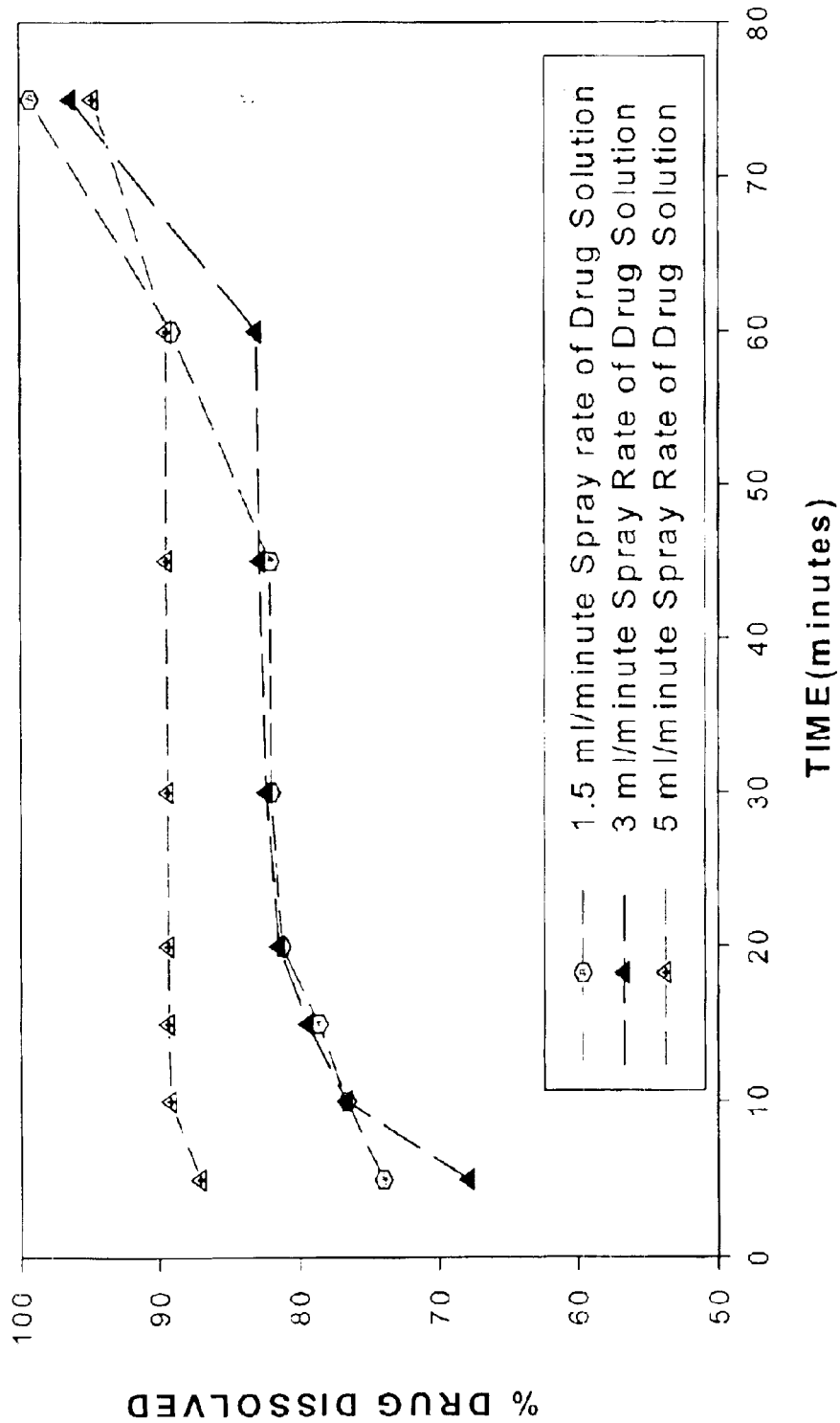
FIG. 21 is a graph showing the dissolution profiles of tablets prepared using drug-lactose mixtures obtained according to a method of the present invention at three different drug deposition rates (i.e., three different drug solution spray rates).

These examples also serve to show that a great deal of control can be had over the end product physical characteristics, and indirectly over the performance and use of these materials. Materials from Examples 7, 8 and 9 were used to make pharmaceutical tablets of the drug product. The dissolution performance of these tablets was far superior to the dissolution of tablets that had been made using conventional processes. This can be seen in the dissolution profiles shown in FIGS. 20 and 21. FIG. 20 shows comparative dissolution profiles of tablets prepared using a drug-lactose mixture obtained by supercritical $CO_2$ processing according to a method of the present invention (Example 7) as compared to conventionally processed tablets at time zero and at 12 weeks under standard storage conditions of 40° C. and 75% RH. The tablets containing the supercritical fluid processed material had faster dissolution initially and after 12 weeks under storage conditions. There was no change in the profile for these tablets after storage, showing that stability was improved by the process. FIG. 21 shows a comparison of the dissolution rates of tablets prepared using drug-lactose mixtures obtained by processing according to Examples 7, 8 and 9. FIG. 21 shows a similarity in profiles indicating good process control at different spray rates of drug solution. The slightly higher dissolution rate for the 5 ml/minute spray rate is expected as the SEM photomicrographs show greater contact of drug and binder which can act as a dissolution enhancer. It is believed that at the higher spray rate of 5 ml/minute, the solution first deposits on the carrier particles and precipitation may take place by SFE of the solvent spread over the carrier particles. This precipitation by SFE may result in the formation of a thin coating of precipitated material on the carrier particles as evidenced by FIG. 19. It is believed that at the lower spray rate, some solution droplets may be dried prior to contacting the carrier and spreading over the carrier particles, thereby resulting in the particulate nature of precipitated particles, as evidenced by FIGS. 15 and 16.

We claim:

1. A method for particle precipitation and retention in carrier material comprising the steps of:
    (a)(1) dissolving a solid or semi-solid material in a pressurized gaseous fluid, thereby forming a solution comprising a gaseous fluid solvent and a dissolved solute of solid or semi-solid material or
    (a)(2) dissolving a solid or semi-solid material in a liquid solvent, thereby forming a liquid solution comprising a liquid solvent and a dissolved solute of solid or semi-solid material;
    (b)(1) precipitating particles of the solid or semi-solid material out of the gaseous fluid solution produced in step (a)(1) by introducing the solution into a region of lower pressure or into a region containing an inert gas or
    (b)(2) precipitating particles of the solid or semi-solid material out of the liquid solution produced in step (a)(2) by introducing the solution into either: (1) a region containing a pressurized gaseous fluid in which said liquid solvent is substantially soluble but said solid or semi-solid material is substantially insoluble, or (2) a region into which a pressurized gaseous fluid is subsequently introduced to cause the solubilization of the liquid solvent into the pressurized gaseous fluid and the precipitation of the particles of the solid or semi-solid material;

(c) directing the introduced solution and resulting precipitated particles produced in step (b)(1) or (b)(2) onto or into a mixed bed of carrier material; and (d) retaining and dispersing at least some of the precipitated particles in the carrier material to produce a blend of the solid or semi-solid material particles and carrier material, a granulation of the solid or semi-solid material particles with carrier material, carrier material partially or fully coated with the solid or semi-solid material particles, or mixtures thereof;

and wherein the carrier material in the mixed bed is maintained in a mixed state at least during steps (c) and (d).

2. A method according to claim 1, wherein the precipitated particles of solid or semi-solid material comprise microparticles or nanoparticles of solid or semi-solid material, or mixtures thereof.

3. A method according to claim 1, wherein the solid or semi-solid material is a physiologically active material, an encapsulating material, a moisture protection material, a light protection material, a gas protection material, a diffusion barrier material or a dissolution or dispersion enhancing material.

4. A method according to claim 3, wherein the solid or semi-solid material is a physiologically active material selected from ipratropium bromide, tiotropium bromide, oxytropium bromide and tipranavir.

5. A method according to claim 1 wherein the gaseous fluid is selected from carbon dioxide, nitrous oxide, trifluoromethane, ethane, ethylene, propane, sulfur hexafluoride, propylene, butane, isobutane, pentane, and mixtures thereof.

6. A method according to claim 1 wherein the liquid solvent is selected from water, aliphatic alcohols, acetone, dichloromethane, ethyl acetate, or mixtures thereof.

7. A method according to claim 1, wherein the carrier material is in the form of powder, granulated powder, tablets, capsules or caplets.

8. A method according to claim 7, wherein the carrier material is in the form of a powder comprising microparticles or nanoparticles of carrier material, or mixtures thereof.

9. A method according to claim 1, wherein the carrier material comprises a pharmaceutically acceptable carrier, adjuvant or excipient, or a physiologically active material, or mixtures thereof.

10. A method according to claim 9, wherein the carrier material is a pharmaceutically acceptable carrier, adjuvant or excipient.

11. A method according to claim 1, wherein the mixed bed of carrier material is maintained in a mixed state during steps (c) and (d) by stirring at a rate of about 20 to 1,000 RPM.

12. A method according to claim 1, wherein step (d) produces a blend of solid or semi-solid material particles with carrier material.

13. A method according to claim 12, wherein the blend of solid or semi-solid material particles with carrier material produced in step (d) comprises a uniform or non-uniform mixture of carrier material, discrete particles of solid or semi-solid material, and carrier material having solid or semi-solid material loosely adhered thereto.

14. A method according to claim 1, wherein step (d) produces a granulation of solid or semi-solid material particles with carrier material.

15. A method according to claim 1, wherein step (d) produces at least some carrier material partially or fully coated with solid or semi-solid material particles.

16. A method according to claim 15, further comprising coating the coated carrier material produced in step (d) by performing a further coating method of claim 15 one or more times on said coated carrier material, wherein the solid or semi-solid material used in the initial and subsequent coating methods may be the same or different during each coating method.

17. A method according to claim 1, wherein said method comprises steps (a)(1), (b)(1), (c) and (d), as defined in claim 1.

18. A method according to claim 17, wherein in step (b)(1), the gaseous fluid solution is introduced into a region of lower pressure.

19. A method according to claim 1, wherein said method comprises steps (a)(2), (b)(2), (c) and (d), as defined in claim 1.

20. A method according to claim 19, wherein in step (b)(2) the liquid solution is introduced into a region containing a pressurized gaseous fluid.

21. A method according to claim 19, wherein in step (b)(2) the liquid solution is introduced into a region into which a pressurized gaseous fluid is subsequently introduced.

22. A method according to claim 1, comprising the steps of:

(a) dissolving a solid or semi-solid physiologically active material in a pressurized gaseous fluid, thereby forming a solution comprising pressurized gaseous fluid solvent and dissolved physiologically active material;

(b) precipitating microparticles and/or nanoparticles of the physiologically active material out of the gaseous fluid solution produced in step (a) by introducing the solution through an orifice into a region of lower pressure;

(c) directing the introduced solution and resulting microparticles and/or nanoparticles produced in step (b) onto or into a mixed bed of powdered carrier material, said powdered carrier material comprising microparticles and/or nanoparticles of a pharmaceutically acceptable carrier, adjuvant or excipient; and (d) retaining and dispersing at least some of the microparticles and/or nanoparticles produced in step (b) in the powdered carrier material to produce a blend of the physiologically active material particles and carrier material, a granulation of the physiologically active material particles with carrier material, carrier material partially or fully coated with the physiologically active material, or mixtures thereof;

and wherein the carrier material in the mixed bed is maintained in a mixed state at least during steps (c) and (d).

23. A method according to claim 22, wherein: the pressurized gaseous fluid is pressurized carbon dioxide; the carrier material is lactose; the orifice through which the gaseous fluid solution is introduced is located within the mixed bed when the mixed bed is at rest; and the mixed bed is maintained in a mixed state at least during steps (c) and (d) by mixing at a speed of about 300 to 1,000 RPM.

24. A method according to claim 1, comprising the steps of:

(a) dissolving a solid or semi-solid physiologically active material in a liquid solvent, thereby forming a solution comprising a liquid solvent and a dissolved physiologically active material;

(b) precipitating microparticles and/or nanoparticles of the physiologically active material out of the liquid solution produced in step (a) by introducing the solution through an orifice into either: (1) a region containing pressurized gaseous fluid in which said liquid solvent is substantially soluble but said physiologically active material is substantially insoluble, or (2) a region into which a pressurized gaseous fluid is subsequently introduced to cause the solubilization of the liquid solvent into the pressurized gaseous fluid and the precipitation of said microparticles and/or nanoparticles;

(c) directing the introduced solution and resulting microparticles and/or nanoparticles produced in step (b) onto or into a mixed bed of powdered carrier material, said powdered carrier material comprising microparticles and/or nanoparticles of a pharmaceutically acceptable carrier, adjuvant or excipient; and (d) retaining at least some of the microparticles and/or nanoparticles produced in step (b) in the powdered carrier material to produce a blend of the physiologically active material particles and carrier material, a granulation of the physiologically active material particles with carrier material, carrier material partially or fully coated with physiologically active material, or mixtures thereof;

and wherein the carrier material in the mixed bed is maintained in a mixed state at least during steps (c) and (d).

25. A method according to claim 24, wherein: the liquid solvent is an aliphatic alcohol, the liquid solution is sprayed through an orifice into a region containing a pressurized gaseous fluid, wherein the orifice is located within the mixed bed when the mixed bed is at rest; and the mixed bed is maintained in a mixed state at least during steps (c) and (d) by mixing at a speed of about 300 to 1,000 RPM.

26. A method according to claim 25, wherein a solid or semi-solid physiologically active material and a solid or semi-solid binder material are both dissolved in the liquid solution in step (a); the liquid solvent is methanol or ethanol; the pressurized gaseous fluid is pressurized carbon dioxide; and the carrier material is lactose.

* * * * *